United States Patent
Willemsen

(10) Patent No.: US 9,512,231 B2
(45) Date of Patent: Dec. 6, 2016

(54) CROSS-LINKING POLYPEPTIDE THAT INDUCES APOPTOSIS

(75) Inventors: Ralph Alexander Willemsen, Rotterdam (NL); Maria Johanna J. E. Van Driel, legal representative, Rotterdam (NL)

(73) Assignee: APO-T B.V., Amersfoort (NL)

( * ) Notice: Subject to any disclaimer, the term of this patent is extended or adjusted under 35 U.S.C. 154(b) by 94 days.

(21) Appl. No.: 13/976,952

(22) PCT Filed: Dec. 22, 2011

(86) PCT No.: PCT/NL2011/050893
§ 371 (c)(1),
(2), (4) Date: Nov. 12, 2013

(87) PCT Pub. No.: WO2012/091564
PCT Pub. Date: Jul. 5, 2012

(65) Prior Publication Data
US 2014/0120090 A1    May 1, 2014

Related U.S. Application Data

(60) Provisional application No. 61/460,213, filed on Dec. 27, 2010, provisional application No. 61/572,318, filed on Jul. 13, 2011.

(51) Int. Cl.
*C07K 16/30* (2006.01)
*C07K 16/28* (2006.01)
*A61K 39/00* (2006.01)

(52) U.S. Cl.
CPC .......... *C07K 16/30* (2013.01); *C07K 16/2833* (2013.01); *A61K 2039/505* (2013.01); *C07K 2317/24* (2013.01); *C07K 2317/32* (2013.01); *C07K 2317/34* (2013.01); *C07K 2317/35* (2013.01); *C07K 2317/60* (2013.01); *C07K 2317/62* (2013.01); *C07K 2317/73* (2013.01); *C07K 2319/00* (2013.01)

(58) Field of Classification Search
CPC ........................... C07K 16/30; C07K 16/2833
USPC .......................... 424/134.1; 530/387.3, 391.7
See application file for complete search history.

(56) References Cited

U.S. PATENT DOCUMENTS

| | | |
|---|---|---|
| 2007/0140966 A1 | 6/2007 | Chang et al. |
| 2009/0208502 A1 | 8/2009 | Willemsen |
| 2009/0269277 A1 | 10/2009 | Chang et al. |
| 2010/0228007 A1* | 9/2010 | Hoogenboom .... C07K 16/2833 530/387.9 |
| 2011/0110851 A1 | 5/2011 | Chang et al. |
| 2014/0205599 A1* | 7/2014 | Willemsen ......... C07K 16/2833 424/134.1 |
| 2014/0227273 A1* | 8/2014 | Willemsen ......... C07K 14/7051 424/135.1 |
| 2015/0056198 A1* | 2/2015 | Renes ................ C07K 16/2833 424/134.1 |

FOREIGN PATENT DOCUMENTS

| | | | |
|---|---|---|---|
| WO | | 2004050705 A2 | 6/2004 |
| WO | WO 2004/003019 | * | 6/2004 |
| WO | | 2007073147 A1 | 6/2007 |
| WO | | 2012091563 A1 | 7/2012 |
| WO | | 2012091564 A2 | 7/2012 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
PCT International Search Report, PCT/NL2011/050893 dated Jun. 6, 2012.

* cited by examiner

*Primary Examiner* — Lynn Bristol
(74) *Attorney, Agent, or Firm* — TraskBritt, P.C.

(57) ABSTRACT

The disclosure relates to a polypeptide comprising at least four domains specifically binding to a certain MHC peptide complex, the domains separated by linker amino acid sequences, thereby providing each domain with the capability to bind a separate MHC peptide complex, to a nucleic acid encoding for such a polypeptide, to a vector comprising such a nucleic acid, to a host cell for expression of such a polypeptide, to a pharmaceutical composition comprising such a polypeptide, and to a kit of parts comprising at least two polypeptides according to the disclosure.

9 Claims, 8 Drawing Sheets

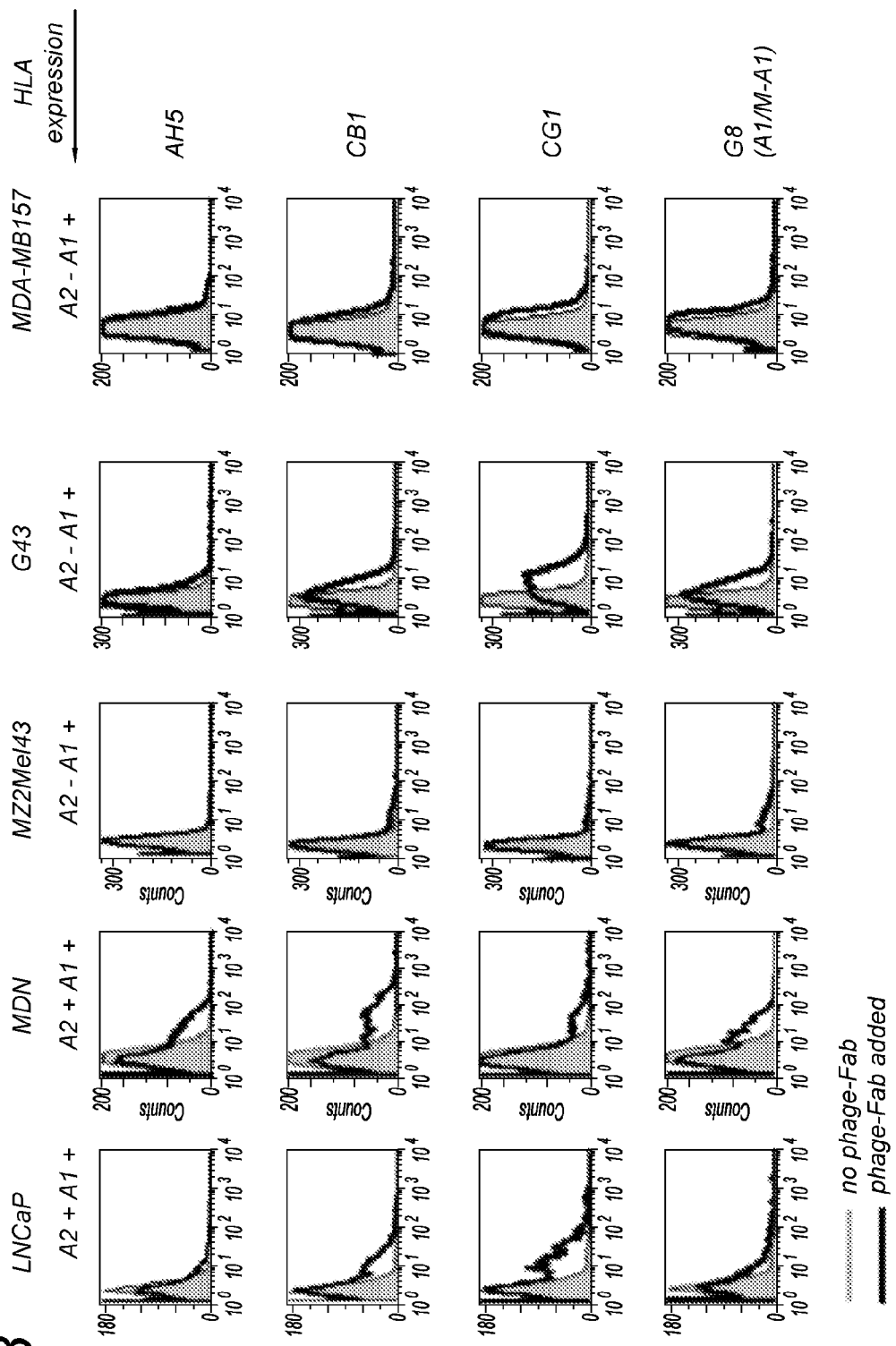

Non-treated          Hexa-AH5

*Fig. 12*
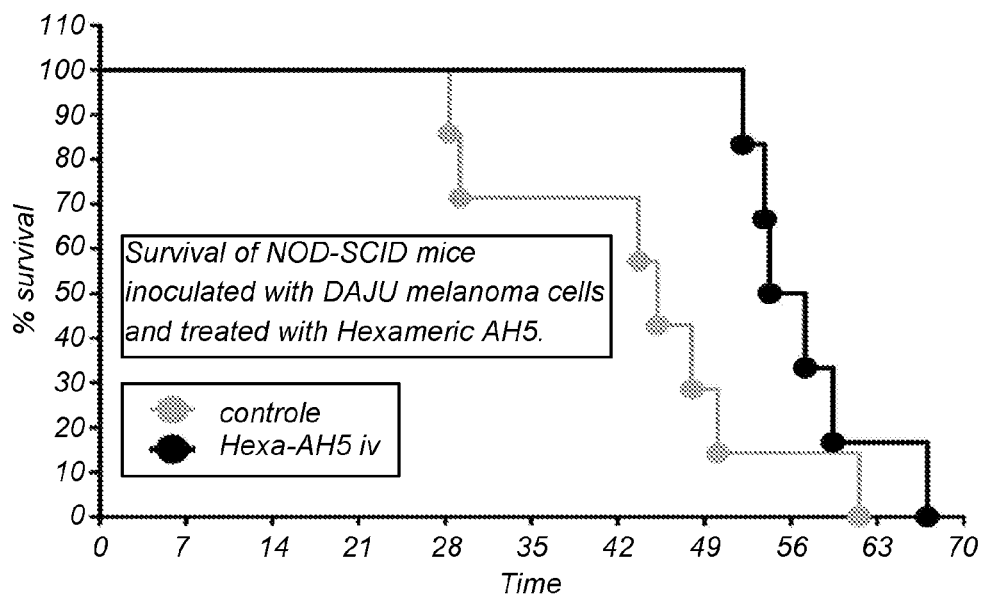
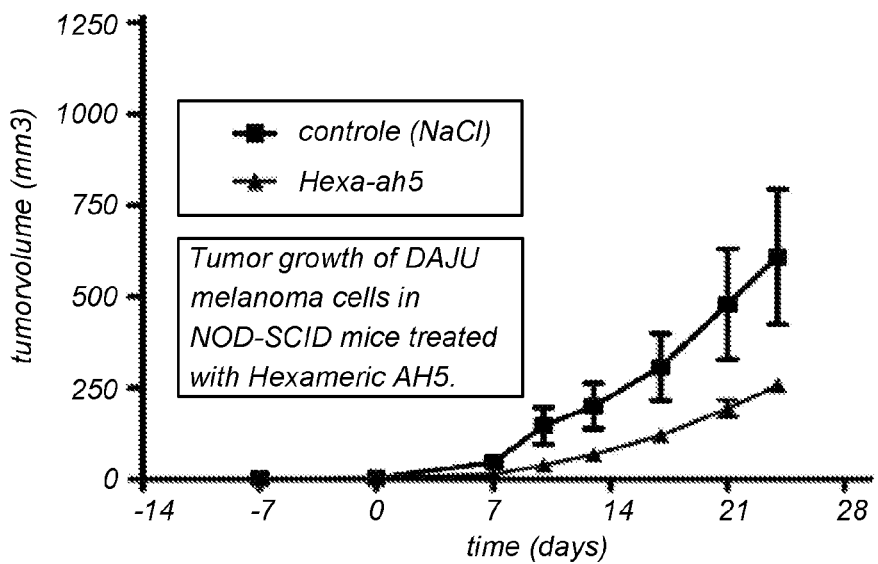

CROSS-LINKING POLYPEPTIDE THAT INDUCES APOPTOSIS

CROSS-REFERENCE TO RELATED APPLICATION(S)

This application is a national phase entry under 35 U.S.C. §371 of International Patent Application PCT/NL2011/050893, filed Dec. 22, 2011, designating the United States of America and published in English as International Patent Publication WO2012/091564 A2 on Jul. 5, 2012, which claims the benefit under Article 8 of the Patent Cooperation Treaty to U.S. Application Ser. No. 61/460,213, filed Dec. 27, 2010 and Application Ser. No. 61/572,318, filed Jul. 13, 2011.

TECHNICAL FIELD

The invention relates to the field of biotherapeutics. It also relates to the field of tumor biology. More in particular, the invention relates to specific binding molecules that induce apoptosis in tumor cells. More specifically, single-chain multivalent, preferably tetravalent or bigger, specifically hexavalent repeats of human antibody variable (heavy) fragments are provided that apparently cross-link MHC-peptide complexes on cells thereby inducing cell death. The invention also relates to the use of these binding molecules in selectively killing cancer cells and other aberrant cells.

BACKGROUND

Since the sixties of the last century it has been proposed to use the specific binding power of the immune system (T-cells and antibodies) to selectively kill tumor cells but leave alone the normal cells in a patient's body. Many tumor antigens that could be targeted by in particular antibodies, like carcino-embryonic antigen (CEA), alpha-fetoprotein (AFP) and so on have been suggested since those days, but for essentially all of these antigens expression is associated with normal tissue as well. Thus, so far this has been an elusive goal.

In an earlier application WO2007/073147 (Apoptosis-inducing protein complexes and therapeutic use thereof incorporated herein by reference) disclosed is a polypeptide complex comprising at least six polypeptides in which polypeptides were assembled to form the complex via post-translational covalent or non-covalent non-peptide bond based linker chemistry. Although such a complex achieves the goal of (specifically) killing, e.g., tumor cells by inducing apoptosis in these tumor cells (although not wishing to be bound by theory, at present it is believed that this is the result of cross-linking), it is quite difficult to produce, since it requires post-translational assembly of polypeptides in functional complexes after expression thereof. In addition the stability of such a complex in vivo may be an issue of concern.

DISCLOSURE

Disclosed herein is the goal of killing aberrant (tumor) cells by apoptosis can be achieved by providing a single-chain polypeptide comprising at least four domains specifically binding to a certain major histocompatibility complex (MHC)-peptide complex, the domains preferably separated by linker amino acid sequences of which the peptide backbone is incorporated in the peptide backbone of the polypeptide, thereby providing each domain with the capability to bind a separate MHC-peptide complex. More specifically, the disclosure relates to multiple recombinant antibody-fragments assembled at the DNA level into a single chain, which specifically bind MHC-peptide complexes and are able to induce cell-death, in particular apoptosis upon cross-linking of multiple MHC-peptide complexes. In particular, the invention relates to methods of diagnosing and treatment of cancer using these recombinant multivalent single-chain polypeptides.

Introduction

The primary immunological function of MHC molecules is to bind and "present" antigenic peptides to form an MHC-peptide (MHC-p) complex on the surface of cells for recognition and binding by antigen-specific T-cell receptors (TCRs) of lymphocytes. With regard to their function, two classes of MHC-peptide complexes can be distinguished:

(i) MHC class I-peptide complexes can be expressed by almost all nucleated cells in order to attract $CD8^+$ cytotoxic T-cells, and (ii) MHC class II peptide complexes are constitutively expressed only on so-called antigen presenting cells (APCs), such as B-lymphocytes, macrophages or dendritic cells (DCs).

MHC class I-peptide complexes are composed of a variable heavy chain, invariable β-microglobulin and antigenic peptide. The MHC class II molecules are characterized by distinctive α and β polypeptide subunits that combine to form αβ heterodimers characteristic of mature MHC class II molecules. Differential structural properties of MHC-class I and -class II molecules account for their respective roles in activating different populations of T-lymphocytes. Cytotoxic $T_C$ lymphocytes (CTLs) bind antigenic peptides presented by MHC class I molecules. Helper $T_H$ lymphocytes bind antigenic peptides presented by MHC class II molecules. MHC class I and class II molecules differentially bind CD8 and CD4 cell adhesion molecules. MHC class I molecules are specifically bound by CD8 molecules expressed on cytotoxic $T_C$ lymphocytes, whereas MHC class II molecules are specifically bound by CD4 molecules expressed on helper $T_H$ lymphocytes.

The sizes of the antigenic peptide-binding pockets of MHC class I and class II molecules differ; class I molecules bind smaller antigenic peptides, typically 8-10 amino acid residues in length, whereas class II molecules bind larger antigenic peptides, typically 13-18 amino acid residues in length.

In humans, MHC molecules are termed human leukocyte antigens (HLA). HLA-associated peptides are short, encompassing typically 9-25 amino acids. Humans synthesize three different types of class I molecules designated HLA-A, HLA-B, and HLA-C. Human class II molecules are designated HLA-D, e.g., HLA-DR.

The MHC expressed on all nucleated cells of humans and of animal cells plays a crucial role in immunological defense against pathogens and cancer. The transformation of normal cells to aberrant cancer cells involves several major changes in gene expression. This results in profound changes in the antigenic composition of cells. It is well established that new antigenic entities are presented as MHC-restricted tumor associated antigens. As such, the MHC class I and class II system may be seen as nature's proteomic scanning chip, continuously processing intracellular proteins, generating antigenic peptides for presentation on the cell surface. If these antigenic peptides elicit an immune reactivity the transformed cells are killed by the cellular immune system. However, if the transformed cells resist immune mediated cell killing, cancer may develop.

Antibodies that bind MHC class I molecules on various cell types have been studied in detail for their mode of action. Mouse monoclonal antibodies, that bind the MHC class I α1 domain of the MHC class I α chain induce apoptosis in activated T-cells, but not in resting T-cells. Other reports mention antibodies specific for, e.g., the α3 domain of MHC class I, which induce growth inhibition and apoptosis in B-cell derived cancer cells. However, in this case a secondary, cross-linking antibody was required for the induction of apoptosis (A. E. Pedersen et al., *Exp. Cell Res.* 1999, 251:128-34).

Antibodies binding to β2-microglobulin (β2-M), an essential component of the MHC class I molecules, also induce apoptosis. Several hematologic cancer cells treated with anti-β2M molecules were killed efficiently, both in vitro and in vivo (Y. Cao et al., *Br. J. Haematol.* 2011, 154:111-121).

Thus, it is known that binding of MHC class I or MHC class II molecules by several anti-MHC antibodies can have an apoptosis-inducing effect. However, the therapeutic application of the currently available anti-MHC antibodies has been hampered by the lack of target cell specificity. Since known antibodies are directed primarily against an epitope of the MHC molecule itself (e.g., HLA-DR), the cell surface expression of the MHC epitope determines whether or not a cell can be triggered to undergo apoptosis. Because MHC class I and MHC class II molecules are expressed on both normal and diseased cells, it is clear that these antibodies cannot discriminate between normal and abnormal (e.g., tumor and/or aberrant) cells. As a consequence, their therapeutic value is significantly reduced if not abolished by the side-effects caused by unwanted apoptosis of healthy cells. According to the invention, antibodies that specifically recognize MHC-presented peptides derived from cancer antigens, on the surface of aberrant cells would therefore dramatically expand the therapeutic repertoire, if they could be shown to have anti-cancer cell activity, leading to the eradication of cancer. In addition, methods to induce apoptosis via MHC-class I or MHC class II, according to the invention, may depend on external cross-linking of anti-MHC antibodies.

Obtaining antibodies binding to MHC-peptide complexes remains a laborious task and several failures have been reported. The first available antibodies have been obtained after immunization of mice with recombinant MHC-peptide complexes or peptide-loaded TAP-deficient antigen presenting cells, and more recently by selection from phage-antibody libraries made from immunized transgenic mice or by selection from completely human antibody phage libraries. Immunization with MHC-peptide complexes is extremely time-consuming. Moreover, antibodies of murine origin cannot be used repetitively in patients because of the likely development of a human anti-mouse antibody response (so-called anti-drug antibodies, ADA). Antibodies derived from phage display in general display low affinity for the antigen and thus may require additional modifications before they can be used efficiently. According to the invention, the antibody specificities are preferably selected through phage (or yeast) display, whereby an MHC molecule loaded with a cancer related peptide is presented to the library. Details are given in the experimental part. It is also possible to employ (transgenic) mice to obtain domains specifically recognizing the MHC-peptide complex. It has been reported that a single chain MHC-peptide molecule can be produced mimicking the peptide MHC complex. E.g., mice having part of a human immune system can be immunized with such a single chain molecule. The antibody specificities, according to the invention, are checked for specificity to the MHC-peptide complex and should not recognize (to any significant extent) empty MHC (although this is less relevant since at least empty MHC-1 is not stable) or MHC loaded with irrelevant peptides or the peptides by themselves.

It is a goal of the disclosure to at least partially overcome the above listed limitations and provide a pharmaceutically active molecule that specifically and efficiently induces cell death, in particular apoptosis and that at the same time is manufactured in a less cumbersome manner, i.e., as a multivalent single-chain protein. In particular, it is a goal of the disclosure to specifically and selectively induce apoptosis of cells of interest, for example, of aberrant cells like tumor cells and/or autoimmune disease related aberrant cells expressing a tumor antigen, leaving healthy cells essentially unaffected. MHC-1 peptide complexes are a valuable target for tumors of almost any origin, whereas MHC-2 peptide complexes are valuable targets for tumors of hematopoietic origin. In addition to tumors, MAGE expression has also been shown in cells involved in Rheumatoid Arthritis (D. K. McCurdy et al., *J. Rheumatol.* 2002, 29:2219-2224).

Provided is a polypeptide comprising at least four domains specifically binding to a certain MHC-peptide complex, the domains separated by linker amino acid sequences, thereby providing each domain with the capability to bind a separate MHC-peptide complex. Typically, a single polypeptide comprising all necessary MHC-peptide complex-binding domains separated by amino acid sequences is provided. This does not mean that every molecule hereof may only consist of a single polypeptide chain binding to MHC-peptide alone. It is, e.g., possible to provide other binding domains with non-MHC-peptide specificity on the single chain polypeptide comprising the MHC-peptide complex binding domains. The second binding domain would typically not comprise antibody-derived binding domains like the first domains, but would be a domain conferring other desirable properties on the binding polypeptide, such as, but not limited to, improved half-life. As an example, the addition of Human Serum Albumin (HSA) on the binding polypeptide may be useful for extension of half-life, etc. The molecules hereof may also comprise a binding domain for molecules, such as HSA, so that HSA may be bound afterwards.

Although not wishing to be bound to theory, it does seem that the MHC-peptide complex binding domains result in a close co-localization (referred to herein as cross-linking) of several MHC-1 molecules (in the present specification most of the time MHC-1 will be mentioned. The disclosure is equally applicable with MHC-2) on the cell membrane, which in turn leads to cell death. The number of MHC-1 molecules that need to be co-localized may vary, but consistent results have been seen with four MHC-peptide complex binding domains in the binding molecule and upward.

The MHC-peptide complex binding domains on the polypeptide may be identical or different, but for specificity's sake, most of them must recognize the complex of MHC-1 loaded with a relevant peptide. The requirement is a functional one. The polypeptides hereof must be able to cross-link MHC-1 loaded molecules on tumor cells, but should not cross-link MHC-1 molecules loaded with a different non-tumor associated peptide or MHC-1 on a normal cell to any significant extent. It is, therefore, preferred that all MHC-peptide complex binding domains recognize the same MHC-1-peptide complex (and essentially only in tumor associated peptide loaded form). For ease of selection and production, the MHC-peptide complex binding domains are preferably identical. If they are not identical, they preferably recognize the same epitope, or at least the same MHC-1-peptide complex. A binding domain must at least be capable of specifically binding to the MHC-1-peptide complex with sufficient affinity to result in binding to essentially only the MHC-1 peptide complexes they were developed against. Many MHC-peptide complex binding domains are well known to people of skill in the art. Immediately apparent are MHC-peptide complex binding domains derived from the immune system, such as single chain T-cell receptor domains and immunoglobulin domains and fragments of immunoglobulins. Preferably, the domains and fragments are 100 to 150 amino acids long. Preferably, the MHC-peptide complex binding domains are similar to variable heavy domains or light domains (Vh or Vl) of antibodies. A good source for such MHC-peptide complex-binding domains are phage display libraries. In another embodiment of the invention, at least one of the specific binding domains comprises a single chain T-cell receptor domain.

Throughout the specification, the term "fragment" refers to an amino acid sequence, which is part of a protein domain or which builds up an intact protein domain. Fragments, according to the invention, must have binding specificity for the respective target.

The techniques of connecting proteinaceous domains in a single molecule are many and well known. Whether the MHC-peptide complex binding domains, from now on also referred to as "binding domains" throughout the specification, are actually selected from a library physically or whether only the information (sequence) is only used is of little relevance.

The binding domains on the polypeptide are typically separated by a linker amino acid sequence, although binding domains in which some amino acids on the boundaries are not involved in binding the target are present (flanking sequences) may not require linkers. The linkers between the binding domains may be the same or different. In many instances, simple Gly-Ser linkers of 4-15 amino acids may suffice, but if greater flexibility of the amino acid chain is desired longer or more complex linkers may be used. Preferred linkers are $(Gly_4Ser)_n$(SEQ ID NO:18), (GST-SGS)$_n$ (SEQ ID NO:19), GSTSGSGKPGSGEGSTKG (SEQ ID NO:20), EFAKTTAPSVYPLAPVLESSGSG (SEQ ID NO:21) or any other linker that provides flexibility for protein folding and stability against protease. Another group of preferred linkers are linkers based on hinge regions of immunoglobulins. These linkers tend to be quite flexible and quite resistant to proteases. Examples are given in the experimental part. The most preferred linkers are EPKSCD-KTHT (IgG1) (SEQ ID NO:22), ELKTPLGDTTHT (IgG3) (SEQ ID NO:23), and ESKYGPP (IgG4) (SEQ ID NO:24). The binding domains may be separated only by a linker, but other useful amino acid sequences may be introduced between the binding domains or at the N-terminus or at the C-terminus of the first or last binding domain sequence, respectively. Thus, in one embodiment, provided is a polypeptide as given above, further comprising an amino acid sequence having an additional function, preferably an effector function. Although one of the advantages of the disclosure is ease of production and the simplicity of the molecules of the invention, the choice for a single nucleic acid encoding all necessary functions in itself enables the relatively easy addition (to the extent that there is room in the chosen expression vectors, etc.) of other functionalities in the resulting polypeptide. The possibilities are many. It is possible to introduce an effector molecule, e.g., a payload, such as a toxin or an apoptosis inducing molecule. It is at present not known how many cross-linked MHC-1 peptide complexes are necessary per cell to induce apoptosis. If only one cross-linked complex would suffice then a payload may be not really be useful. If more than one cross-linked complex is necessary then a payload may be helpful in those cases where the cell has been reached by the molecule, but not enough cross-linked complexes are formed. In that case, if and when the cross-linked complex is internalized (as is expected) then the payload can have its (cytotoxic) function. It is preferred that such a payload has a contribution to the specificity of the cytotoxic effect. Therefore, it is preferred to use as a payload a polypeptide that induces cell death in aberrant cells, but not in normal cells. Such a polypeptide is apoptin or a number of its fragments and/or derivatives. Other examples of cytotoxic polypeptides include, but are not limited to, cholera toxin, ricin A, etc., other functions that may be introduced may have to do with improved half-life (HSA can be included) or complement activation (Fc part of immunoglobulins, in this case the molecules, according to the invention, may dimerize). Other functionalities that can be incorporated are cytokines, hormones, Toll-like receptor ligands, etc.

The number of binding domains necessary to provide sufficient cross-linking will undoubtedly vary with the tumor that it is targeted. Different tumors will have different levels of MHC-1/MHC-2 expression, different levels of peptide presentation, etc. It is expected that 4-12 binding domains per polypeptide chain will be optimal. There is however no real upper limit, except for tissue penetration, expression and production issues. For ease of production, hexamers (which have shown excellent results in animal models) are preferred. Therefore, the invention provides a polypeptide, according to the invention, having six MHC-peptide complex binding domains.

As stated before, the binding domains are preferably based on, or derived from immunoglobulin domains or fragments of domains (or comparable single chain T-cell receptor domains or other binding proteins). The immunoglobulin domains should have at least one CDR-like domain or one domain comprising one or more CDR-like loops, preferably, however, three domains. These CDR-like domains should be separated by (framework) domains that present the CDR-like regions in a proper manner. A suitable domain is a Vh domain of a human antibody. This domain may be "camelized," meaning that a number of amino acid residues have been replaced by amino acid residues from camelids, such as in the llama Vh. Preferred substitutions are E6A, A33C, V37F, G44E, L45R, W47G, S74A, R83K, A84P or L108Q. Thus, the invention provides a polypeptide, according to the invention, wherein at least one, but preferably all of the specific binding domains comprise an immunoglobulin fragment. The origin or the method of selection as well as the method of production of the immunoglobulin fragments to be used in the polypeptides, according to the disclosure is not really relevant. According to one embodiment, a polypeptide comprises at least one, preferably more than one, immunoglobulin fragment that is a natural, mutated and/or synthetic VH.

Although many different combinations of MHC and peptides are contemplated, the most preferred is the combination of MHC-1 and a peptide from a tumor related antigen presented by the MHC-1. Because of HLA restrictions, there are many combinations of MHC-1 peptide complexes as well as MHC-2 peptide complexes that can be designed based on the rules for presentation of peptides in MHC. These rules include size limits on peptides that can be presented in the context of MHC, restriction sites that need to be present for processing of the antigen in the cell, anchor sites that need to be present on the peptide to be presented, etc. The exact rules differ for the different HLA classes and for the different MHC classes. It is found that MAGE peptides are very suitable for presentation in an MHC context. An MHC-1 presentable peptide with the sequence Y-L-E-Y-R-Q-V-P-G (SEQ ID NO:7) in MAGE-A was identified, that is present in almost every MAGE-A variant; MAGE-A1-MAGE-A12, and that will be presented by one of the most prevalent MHC-1 alleles in the Caucasian population (namely, HLA-A0201). A second MAGE peptide that is presented by another MHC-1 allele (namely, HLA-CW7) and that is present in many MAGE variants, like, for example, MAGE-A2, -A3, -A6 and -A12, is E-G-D-C-A-P-E-E-K (SEQ ID NO:8). These two combinations of MHC-1 and MAGE peptides together would cover 80% of the Caucasian population. It is shown, in vitro, that tumor cell lines with the correct HLA alleles present are efficiently killed by the molecules. The same approach can be followed for other MHC molecules, other HLA restrictions and other tumor-associated antigens. Relevant is that the chosen peptide to elicit the response must be presented in the context of an MHC molecule and recognized in that context only. Furthermore, the peptide must be derived from a sufficiently tumor-specific antigen and the HLA restriction must occur in a relevant part of the population. One of the important advantages of the disclosure is that tumors that down-regulate their targeted MHC-peptide complex, can be treated with a second binding molecule against a different MHC-peptide complex based on the same antigen. If this one is down-regulated a third one will be available. For heterozygotes, six different targets on MHC may be available. Since cells need to be "inspected" by the immune system from time to time, escape through down-regulation of all MHC molecules does not seem a viable escape route. In the case that MAGE is the antigen from which the peptide is derived escape through down-regulation of the antigen is also not possible, because MAGE seems important for survival of the tumor (L. Marcar et al., *Cancer Res.* 2010, 70:10362-10370). Thus, the disclosure, in an important aspect reduces or even prevents escape of the tumor from the therapy, in the sense that the tumor remains treatable.

Because MHC molecules are used as a target, and individuals differ in the availability of MHC targets, also provided is a so-called companion diagnostic to determine the HLA composition of an individual. Although the disclosure preferably uses a more or less universal (MAGE) peptide, it also provides a diagnostic for determining the expression of the particular antigen by the tumor. In this manner, the therapy can be geared to the patient, particularly also in the set-up to prevent escape, as described herein before. It is known that the HLA restriction patterns of the Asian population and the black population are different than that of the Caucasian population. For these populations, different MHC-peptide complexes can be targeted, as described in the detailed description.

Although the present specification presents more specific disclosure on tumors, it must be understood that other aberrant cells can also be targeted by the molecules of the disclosure. These other aberrant cells are typically cells that also proliferate without sufficient control. This occurs in autoimmune diseases. It is typical that these cells start to show expression of tumor antigens. In particular, MAGE polypeptides have been identified in Rheumatoid Arthritis. Thus, the invention provides in a preferred embodiment a polypeptide, according to the invention, whereby the specific binding domains are capable of binding to an MHC-I-peptide complex. In a further preferred embodiment, the invention provides a polypeptide whereby the specific binding domains are capable of binding to MHC-I-peptide complexes comprising a peptide derived from a tumor related antigen, in particular MHC-I-peptide complexes comprising a variety of MAGE peptides.

An "aberrant cell" is defined as a cell that deviates from its usual and healthy normal counterparts and shows uncontrolled growth characteristics.

One of the polypeptides, exemplified herein, has binding domains with the amino acid sequence essentially corresponding to:

```
                                        (SEQ ID NO: 11, AH5)
QLQLQESGGGVVQPGRSLRLSCAASGFTFSSYGMHWVRQAPGKEREGVA

VISYDGSNKYYADSVKGRFTISRDNSKNTLYLQMNSLRAEDTAVYYCAG

GSYYVPDYWGQGTLVTVSS.
```

Another one has binding domains comprising the amino acid sequence:

```
                                        (SEQ ID NO: 12, 11H)
EVQLVQSGGGLVKPGGSLRLSCAASGFTFSDYYMSWIRQAPGKGLEWLS

YISSDGSTIYYADSVKGRFTVSRDNAKNSLSLQMNSLRADDTAVYYCAV

SPRGYYYYGLDLWGQGTTVTVSS.
```

One polypeptide has an amino acid sequence essentially corresponding to:

```
                                        (SEQ ID NO: 4, Hexa-AH5)
MAQLQLQESGGGVVQPGRSLRLSC

AASGFTFSSYGMHWVRQAPGKEREGVAVISYDGSNKYYADSVKGRFTISRDNSKNTLY

LQMNSLRAEDTAVYYCAGGSYYVPDYWGQGTLVTVSSGSTSGSMAQLQLQESGGGVV

QPGRSLRLSCAASGFTFSSYGMHWVRQAPGKEREGVAVISYDGSNKYYADSVKGRFTIS

RDNSKNTLYLQMNSLRAEDTAVYYCAGGSYYVPDYWGQGTLVTVSSGSTSGSMAQLQ

LQESGGGVVQPGRSLRLSCAASGFTFSSYGMHWVRQAPGKEREGVAVISYDGSNKYYA

DSVKGRFTISRDNSKNTLYLQMNSLRAEDTAVYYCAGGSYYVPDYWGQGTLVTVSSGS

TSGSMAQLQLQESGGGVVQPGRSLRLSCAASGFTFSSYGMHWVRQAPGKEREGVAVIS

YDGSNKYYADSVKGRFTISRDNSKNTLYLQMNSLRAEDTAVYYCAGGSYYVPDYWGQ
```

```
GTLVTVSSGSTSGSMAQLQLQESGGGVVQPGRSLRLSCAASGFTFSSYGMHWVRQAPG

KEREGVAVISYDGSNKYYADSVKGRFTISRDNSKNTLYLQMNSLRAEDTAVYYCAGGS

YYVPDYWGQGTLVTVSSGSTSGSMAQLQLQESGGGVVQPGRSLRLSCAASGFTFSSYG

MHWVRQAPGKEREGVAVISYDGSNKYYADSVKGRFTISRDNSKNTLYLQMNSLRAED

TAVYYCAGGSYYVPDYWGQGTLVTVSS.
Or:

(SEQ ID NO: 13, Hexa-11HCH1)
EVQLVQSGGGLVKPGGSLRLSCAASGFTFSDYYMSWIRQAPGKGL

EWLSYISSDGSTIYYADSVKGRFTVSRDNAKNSLSLQMNSLRADDTAVYYCAVSPRGY

YYYGLDLWGQGTTVTVSSEPKSCDKTHTAEVQLVQSGGGLVKPGGSLRLSCAASGFTF

SDYYMSWIRQAPGKGLEWLSYISSDGSTIYYADSVKGRFTVSRDNAKNSLSLQMNSLRA

DDTAVYYCAVSPRGYYYYGLDLWGQGTTVTVSSEPKSCDKTHTAEVQLVQSGGGLVK

PGGSLRLSCAASGFTFSDYYMSWIRQAPGKGLEWLSYISSDGSTIYYADSVKGRFTVSRD

NAKNSLSLQMNSLRADDTAVYYCAVSPRGYYYYGLDLWGQGTTVTVSSEPKSCDKTH

TAEVQLVQSGGGLVKPGGSLRLSCAASGFTFSDYYMSWIRQAPGKGLEWLSYISSDGST

IYYADSVKGRFTVSRDNAKNSLSLQMNSLRADDTAVYYCAVSPRGYYYYGLDLWGQG

TTVTVSSEPKSCDKTHTAEVQLVQSGGGLVKPGGSLRLSCAASGFTFSDYYMSWIRQAP

GKGLEWLSYISSDGSTIYYADSVKGRFTVSRDNAKNSLSLQMNSLRADDTAVYYCAVS

PRGYYYYGLDLWGQGTTVTVSSEPKSCDKTHTAEVQLVQSGGGLVKPGGSLRLSCAAS

GFTFSDYYMSWIRQAPGKGLEWLSYISSDGSTIYYADSVKGRFTVSRDNAKNSLSLQMN

SLRADDTAVYYCAVSPRGYYYYGLDLWGQGTTVTVSSASTKGPSVFPLAPSSKSTSGGT

AALGCLVKDYFPEPVTVSWNSGALTSGVHTFPAVLQSSGLYSLSSVVTVPSSSLGTQTYI

CNVNHKPSNTKVDKKVEPKSC.
Or:

(SEQ ID NO: 17, Hexa-11HAH5)
EVQLVQSGGGLVKPGGSLRLSCAASGFTFSDYYMSWIRQAPGKGLEWLSYISSDGSTIY

YADSVKGRFTVSRDNAKNSLSLQMNSLRADDTAVYYCAVSPRGYYYYGLDLWGQGTT

VTVSSGGGGSGGGGSGGGSQLQLQESGGGVVQPGRSLRLSCAASGFTFSSYGMHWVRQ

APGKEREGVAVISYDGSNKYYADSVKGRFTISRDNSKNTLYLQMNSLRAEDTAVYYCA

GGSYYVPDYWGQGTLVTVSSGSTSGSGKSPGSGEGTKGEVQLVQSGGGLVKPGGSLRL

SCAASGFTFSDYYMSWIRQAPGKGLEWLSYISSDGSTIYYADSVKGRFTVSRDNAKNSL

SLQMNSLRADDTAVYYCAVSPRGYYYYGLDLWGQGTTVTVSSEFAKTTAPSVYPLAPV

LESSGSGQLQLQESGGGVVQPGRSLRLSCAASGFTFSSYGMHWVRQAPGKEREGVAVIS

YDGSNKYYADSVKGRFTISRDNSKNTLYLQMNSLRAEDTAVYYCAGGSYYVPDYWGQ

GTLVTVSSGGGGSGGGGSGGGGSEVQLVQSGGGLVKPGGSLRLSCAASGFTFSDYYMS

WIRQAPGKGLEWLSYISSDGSTIYYADSVKGRFTVSRDNAKNSLSLQMNSLRADDTAV

YYCAVSPRGYYYYGLDLWGQGTTVTVSSGSTSGSGKSPGSGEGTKGQLQLQESGGGVV

QPGRSLRLSCAASGFTFSSYGMHWVRQAPGKEREGVAVISYDGSNKYYADSVKGRFTIS

RDNSKNTLYLQMNSLRAEDTAVYYCAGGSYYVPDYWGQGTLVTVSS
```

The disclosure, of course, comprises the nucleic acid encoding the polypeptides. The molecules can be produced in prokaryotes as well as eukaryotes. The codon usage of prokaryotes may be different from that in eukaryotes. The nucleic acids can be adapted in these respects. Also, elements that are necessary for secretion may be added, as well as promoters, terminators, enhancers, etc. In addition, elements that are beneficial or necessary for isolation and/or purification may be added. Typically, the nucleic acids are provided in an expression vector suitable for the host in which they are to be produced. Choice of a production platform will depend on the size of the molecule, the expected issues around folding, whether additional sequences are present that require glycosylation, etc., thus, typically, nucleic acids are adapted to the production platform in which the polypeptides are to be produced. Thus, provided is a nucleic acid encoding a polypeptide as well as an expression vector comprising such a nucleic acid. For stable expression in a eukaryote it is preferred that the nucleic acid encoding the polypeptide is integrated in the host cell genome (at a suitable site that is not silenced). Thus, the disclosure comprises in a particular embodiment: a vector comprising means for integrating the nucleic acid in the genome of a host cell.

Further described is the host cell or the organism in which the polypeptide encoding nucleic acid is present and which is capable of producing the polypeptide.

Included in the disclosure are also the methods for producing a polypeptide comprising culturing a host cell comprising a nucleic acid allowing for expression of the nucleic acid and harvesting a polypeptide.

For administration to subjects, the polypeptides are formulated. Typically, these polypeptides will be given parenterally. For formulation, simply water (saline) for injection may suffice. For stability reasons more complex formulations may be necessary. Also contemplated are lyophilized compositions as well as liquid compositions, provided with the usual additives. Thus, provided is a pharmaceutical composition comprising a polypeptide and suitable diluents and/or excipients.

The dosage of the polypeptides is established through animal studies and clinical studies in so-called rising-dose experiments. Animal experiments so far have not shown any relevant toxicity at effective dosages. Typically, the doses will be comparable with present day antibody dosages (at the molar level, the weight of the invented molecules may differ from that of antibodies). Typically, such dosages are 3-15 mg/kg body weight, or 25-1000 mg per dose.

It has been established in the field of tumor therapy that a single agent is hardly ever capable of eradication of tumor from a patient. Especially in the more difficult to treat tumors, the first applications of the polypeptides will (at least initially) probably take place in combination with other treatments (standard care). Thus, also provided is a pharmaceutical composition comprising a polypeptide and a conventional cytostatic and/or tumoricidal agent. Moreover, also provided is a pharmaceutical composition comprising a polypeptide for use in an adjuvant treatment of cancer. Additionally, also provided is a pharmaceutical composition comprising a polypeptide for use in a combination chemotherapy treatment of cancer.

The pharmaceutical compositions hereof will typically find their use in the treatment of cancer, particularly in forms of cancer where the targets of the preferred single-chain polypeptides (complexes of MHC and MAGE-A peptides) are presented by the tumors. Table 1 gives a list of tumors on which these targets have been found. It is easy using a binding domain hereof to identify tumors that present the target MHC-peptide complexes. This can be done in vitro or in vivo (imaging).

The terms "repeat" and "repeats" have the same meaning as "domain" and "domains," respectively, throughout the specification. The term "binding" is defined as interactions between molecules that can be distinguished from background interactions. The term "specific," for example, in "specific binding (domain)," has the meaning of indicating a molecule that can have an interaction with another molecule with higher binding affinity than background interactions between molecules. Typically, the polypeptides hereof do not need high affinity binding domains, since they benefit from the so-called avidity effect. Similarly, the term "specificity" refers to an interaction, for example, between two molecules or between a cell and a molecule that has higher binding affinity than background interactions between molecules.

BRIEF DESCRIPTION OF THE DRAWINGS

FIG. 3: Phages expressing HLA-A2/multi-MAGE-A-specific Fab bind tumor cells of distinct histologic origin. Phages AH5, CB1 and CG1 specific for HLA-A0201/multi-MAGE-A and a positive control phage specific for HA-0101/MAGE-A1 were used for staining of distinct tumor cell lines. To this end the prostate cancer cell line LNCaP, the multiple myeloma cell line MDN, the melanoma cell lines MZ2-MEL43 and G43, and the breast cancer cell line MDA-MD 157 were incubated with the different phages (30 minutes at 4° C.), bound phages were then detected by flow cytometry using anti-phage antibodies and fluorescently labeled secondary antibodies.

FIG. 12: mouse survival and tumor growth after i.v. treatment with hexameric AH5 protein. Melanoma Daju cells were subcutaneously injected into NOD-SCID mice. When palpable tumors were present, mice were intravenously injected with hexameric AH5 (2.5 μg/2 times/week). Tumor growth and survival was determined.

DETAILED DESCRIPTION OF THE INVENTION

Figure 1:
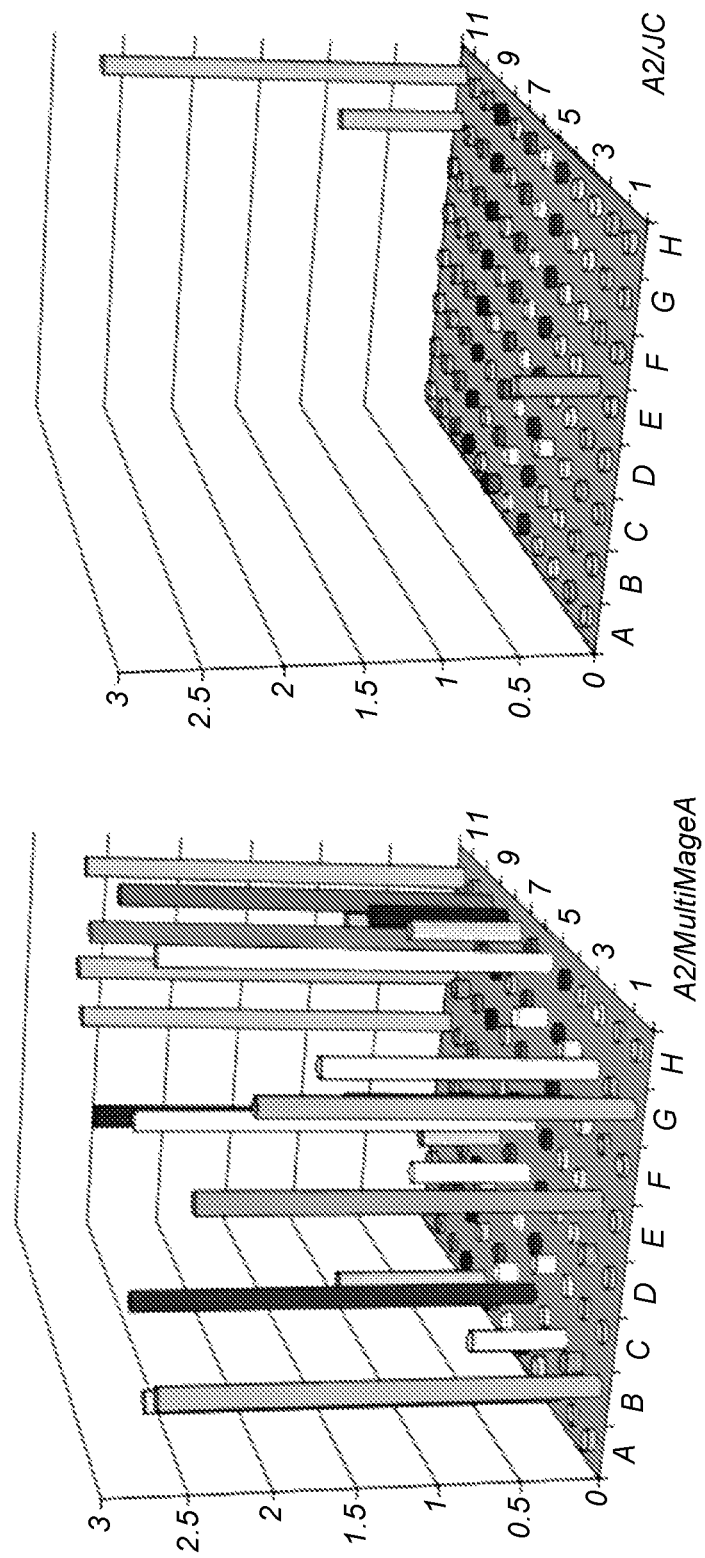
FIG. 1: Specific binding of HLA-A0201/multi-MAGE-A-specific phage clones isolated from a large human non-immune antibody Fab phage library. Individual antibody Fab expressing phages that were selected against biotinylated HLA-A0201/multi-MAGE-A were analyzed by ELISA for their capacity to bind the relevant peptide/MHC complex only. Streptavidin coated 96 well plates were incubated with soluble HLA-A0201/multi-MAGE-A (A2/multiMage) or HLA-A0201/JCV (A2/JC) peptide/MHC complexes (10 µg/ml), washed to remove non-bound complexes and incubated with individual phage clones. Non-binding phages were first removed by three washes with PBS/TWEEN®, followed by incubation with anti-M13 antibody (1 µg/ml, Amersham) for one hour by room temperature. Finally, the wells were incubated with an HRP-labeled secondary antibody and bound phages detected.

As outlined in the previous application WO2007/073147, the desired specific and selective killing of aberrant cells via the apoptosis machinery can be achieved by contacting these cells with a multivalent mono-specific protein complex comprising multiple antigen-specific MHC-restricted single chain T-cell receptors (TCRs) and/or MHC-restricted antigen-specific antibodies, which antigen is expressed by the targeted aberrant cells and presented in the context of MHC molecules. This finding then, opened the possibility to selectively kill a population of cells that are positive for a certain MHC-peptide complex of interest, for example, tumor cells expressing HLA class I molecules in complex with peptides derived from tumor-associated antigens.

Without wishing to be bound by theory, and based on in the disclosure in this application, it is thought that a multivalent like, for example, a hexavalent mono-specific protein induces apoptosis via the clustering of a number of (identical) MHC-p complexes on the cell surface of a target cell. The data shown in the previous application WO2007/073147 suggest that clustering of three MHC-p complexes may not be sufficient for apoptosis induction, whereas a hexavalent complex is very efficient in inducing apoptosis. Thus, it is disclosed now that apoptosis induction requires the binding of at least four, preferably at least five, more preferably at least six MHC-p complexes by one multivalent single-chain protein.

The terms "protein" and "polypeptide" have roughly the same meaning throughout the text of this application and refer to a linear proteinaceous sequence comprising two or more linked amino acid residues. In the context of the proteins and protein complexes that specifically bind to MHC-p complexes, "binding molecules" and "polypeptides" have the same meaning as "protein" and "protein complexes." The term "apoptosis" refers to the process of programmed cell death.

In one embodiment, a multivalent single-chain protein encompasses four, five, six, seven, eight, nine, ten, eleven or twelve domains or clusters of domains, each domain or cluster of domains capable of recognizing and binding to a specific MHC-peptide complex. In contrast to the known methods for apoptosis induction using anti-MHC antibodies, a multivalent single-chain monomeric protein, disclosed herein, can induce apoptosis itself and does not require any external post-translational cross-linking. The multiple domains or multiple clusters of domains are connected to form a linear sequence at the DNA level and thus connected into a linear single-chain monomeric polypeptide via regular peptide bonds at the protein level.

The current invention, therefore, relates to a multivalent single-chain protein comprising at least four and preferably six domains or clusters of domains capable of recognizing and binding to a specific MHC-peptide complex. At least four or preferably six domains or clusters of domains preferably recognize the same MHC-peptide complex, i.e., the preferred multivalent single-chain protein is mono-specific with respect to the MHC-p complex. The domains of the multivalent single-chain protein that specifically recognize and bind to a MHC-p complex can be TCR domains or a functional fragment thereof (together herein referred to as TCRs) and/or an antibody that mimics TCR specificity, for example, a genetically engineered antibody, such as a single-chain variable fragment (scFv) or the variable domain V of the heavy chain H of an antibody (referred to throughout the text as VH, Vh or $V_H$). Also, a multivalent single-chain protein of the invention may encompass TCR domains as well as MHC class-restricted antibody domains, provided that both types of domains recognize essentially the same MHC-peptide antigen. In the specification, "MHC-peptide complex" and "MHC-peptide antigen" have the same meaning. In the context of a peptide that is presented by an MHC molecule, forming an MHC-p complex, the terms "peptide," "peptidic antigen," "antigenic epitope" and "antigenic peptide" refer to the same peptide in the complex.

Multivalent TCR domain complexes and therapeutic applications thereof are known in the art. In application WO2004/050705, a multivalent TCR domain complex comprising at least two TCR domains, linked by a non-proteinaceous polymer chain or a linker sequence composed of amino acid residues, is disclosed. The disclosed use of the TCR complex is in targeting cell delivery of therapeutic agents, such as cytotoxic drugs, which can be attached to the TCR complex. Di-, tri- and tetravalent TCR complexes are disclosed but divalent TCR complexes are preferred. Importantly, complexes of more than four TCRs are not described. Furthermore, WO2004/050705 focuses solely on the use of a multivalent TCR complex for the delivery of a therapeutic agent, e.g., a toxic moiety for cell killing, to a target cell. It does not teach or suggest the apoptosis-inducing capacity of a multivalent TCR complex itself. The antigen-specific MHC-restricted binding capacity of a multivalent monomeric single-chain protein of the current invention is sufficient to induce apoptosis of a target cell expressing the relevant antigen. Therefore, using the sole protein of the invention only is sufficient for obtaining the desired effect. In, for example, application WO2004/050705, the additive use of an additional or attached cytotoxic agent or toxic moiety is, for example, required.

In the previous application WO2007/073147, it is disclosed that separate individual polypeptide monomers that together build up a multivalent complex of that invention, be it antigen-specific MHC-restricted TCRs, TCR-like antibodies or combinations thereof, are post-translationally linked or connected to each other in any suitable manner, be it covalently or non-covalently using standard polypeptide linkage chemistry, in order to achieve the desired pro-apoptotic activity.

According to the current invention, any proteinaceous domain or cluster of domains capable of specifically recognizing and binding to an MHC-peptide complex, comprising either MHC class I or MHC class II proteins, is suitably used in a multivalent apoptosis-inducing single-chain protein. In one embodiment, this protein, according to the invention, comprises at least four, for example, six or even more domains or clusters of domains, connected through regular peptide bonds between the peptide backbone of the domains or clusters of domains building up the multivalent polypeptide, comprising amino acid sequences corresponding to the $V_H$ domains of human antibodies.

The current invention is primarily exemplified by the generation of a hexavalent mono-specific single-chain monomeric protein, which is specific for a tumor antigen. This hexavalent single-chain protein has therapeutic value in the treatment of cancer. Moreover, the skilled person will appreciate that the disclosure is not limited to any type of antigen, and that hexavalent single-chain proteins are provided that can selectively kill target cells, like, for example, selected aberrant cells, expressing any antigen.

Preferably, a polypeptide of the invention is capable of specifically and efficiently recognizing and binding to a cancer-specific epitope or an epitope associated with autoimmune disorders or an epitope presented by any other aberrant cell, for all examples in the context of MHC. Cancer cells may express a group of antigens termed "cancer testis antigens" (CT). These CT are presented as antigenic peptides by MHC molecules (as MHC-p complexes) to CTLs. In fact, these CT are immunogenic in cancer patients as they may elicit anti-cancer responses. They exhibit highly tissue-restricted expression, and are considered promising target molecules for cancer vaccines and other immune intervention strategies.

To date, more than 44 CT gene families have been identified and their expression studied in numerous cancer types. For example, bladder cancer, non-small lung cancer, prostate cancer, melanoma and multiple myeloma express CT genes to a high level. Experiments have shown that expression of these CT genes was indeed testis restricted in healthy individuals. Other antigens that were shown to elicit immune responses in cancer patients include differentiation antigens, such as, for example, the melanoma antigens gp100, Mart-1, Tyrosinase, or antigens that are over-expressed in cancer cells, such as, for example, p53, Her-2/neu, WT-1. Both groups of antigens are not specific for these aberrant cells and are also expressed in healthy tissue, and may therefore elicit autoimmune disease when targeted. In a preferred embodiment, the hexavalent single-chain protein is capable of recognizing and binding to an MHC class I- or to an MHC class II-tumor antigen complex, in particular melanoma associated antigens (MAGE), specifically at tumor cells, leaving healthy cells and tissue essentially unaltered, NB: testis do not present antigens in the context of HLA. The antigen is, for example, a peptide from a member of the CT gene families. The antigen can also be selected from the series of tumor antigens and/or from the series of antigens expressed in the tissue or organ affected by cancer cells, for which it is known that their expression is not tumor specific or not specific for the tissue or organ bearing cancer cells, as is known, for example, for gp100, Mart-1, Tyrosinase, p53, Her-2/neu, WT-1. These antigens are selected as a therapeutic target when the risk for adverse effects is acceptable when related to the beneficial outcome of the treatment with hexavalent single-chain protein, which targets the antigenic peptide complexed with MHC. The general benefit of the disclosure is that, where up until now targets associated with cell surfaces were the predominant goal, intracellular targets now become available through presentation by MHC-1 and/or MHC-2. This means that a renewed survey of intracellular antigens will be carried out to identify intracellular antigens that are tumor specific enough to merit using them as targets in the disclosure. Such a screen has already been carried out in the context of tumor vaccination schemes. Targets that are valuable (because of sufficient specificity, not necessarily efficacy) as tumor vaccine candidates will also be valuable for the disclosure: MAGE-A1, -A2, -A3, -A4, -A5, -A6, -A7, -A8, -A9, -A10, -A11, -A12, -A12, MAGE-B, MAGE-C2, LAGE-1, PRAME, NY-ESO-1, PAGE, SSX-2, SSX-4, GAGE, TAG-1, TAG-2, and HERV-K-MEL.

Human tumor antigens presented by MHC class II molecules have been described, with nearly all of them being associated to multiple myeloma or malignant melanoma. The first antigenic peptide related to a melanoma-specific antigen found was a peptide derived from MAGE-1. Furthermore, three melanoma epitopes were found to originate from the MAGE family of proteins and presented by HLA-DR11 and HLA-DR13. Another set of melanoma antigens, known to contain also MHC class I tumor antigens, comprises Melan-A/MART-1, gp100 and tyrosinase. For an overview of T-cell epitopes that are of use for the disclosure, also see worldwide web at cancerimmunity.org/peptidedatabase/Tcellepitopes.htm.

The first discovered CT, belonging to the group of MAGE-A antigens, has an expression profile that is uniquely restricted to cancer cells and testis cells. However, testis cells are not targeted by the immune system, as they lack expression of MHC molecules. The MAGE-A antigens belong to a family of twelve genes that show high homology. Their expression has been associated with early events in malignant cell transformation and metastatic spread of cancer cells. In addition, down-regulation of MAGE-A expression may induce apoptosis in cancer cells. Within the MAGE-A genes several antigenic epitopes are known by the art. Antigenic peptides usually are presented as 8- or 9-mer amino acid peptides by MHC class I molecules. In addition, antigenic epitopes are known that are present in multiple MAGE-A genes due to the high homology between the different MAGE-A genes. These antigenic epitopes may be considered as multi-MAGE-A epitopes and are presented on cancer cells of various histologic origin. Therefore, they might serve as universal targets for anti-cancer therapy.

MHC molecules are also important as signal-transducing molecules, regulating immune responses. Cross-linking of MHC Class I molecules on B- and T-cells initiates signals that can result in either anergy, or apoptosis, or alternatively in cell proliferation and cytokine production. Several intracellular signaling pathways have been identified that are induced by MHC class I cross-linking. These include 1) phosphorylation of tyrosine kinases, leading to enhanced levels of intracellular calcium ions; 2) activation of the JAK/STAT pathway; and 3) inhibition of PI3K, resulting in the activation of JNK activation. Very high affinity antibodies against MHC that are internalized after binding may induce apoptosis. To be certain in the case of T cell and/or B cell derived tumors, the effect of the molecules may be tested in vitro before initiating therapy.

A further aspect relates to a method for providing the hexavalent single-chain monomeric protein hereof. As described herein above, it typically involves providing a nucleic acid encoding the desired hexavalent polypeptide. This nucleic acid can be introduced, preferably via a plasmid or expression vector, into a prokaryotic host cell and/or in eukaryotic host cell capable of expressing the construct. In one embodiment, a method provides a hexavalent single-chain apoptosis inducing protein comprises the steps of providing a host cell with one or more nucleic acid(s) encoding the hexavalent protein capable of recognizing and binding to a specific MHC-peptide complex, and allowing the expression of the nucleic acids by the host cell.

Preferred host cells are bacteria, like, for example, bacterial strain BL21 or strain SE1, or mammalian host cells, more preferably human host cells. Suitable mammalian host cells include human embryonic kidney (HEK-293) cells or Chinese hamster ovary (CHO) cells, which can be commercially obtained. Insect cells, such as S2 or S9 cells, may also be used using baculovirus or insect cell expression vectors, although they are less suitable when the polypeptides include elements that involve glycosylation. The hexavalent single-chain polypeptides produced can be extracted or isolated from the host cell or, if they are secreted, from the culture medium of the host cell. Thus, in one embodiment, a method comprises providing a host cell with one or more nucleic acid(s) encoding the hexavalent single-chain polypeptide capable of recognizing and binding to a specific MHC-peptide complex, allowing the expression of the nucleic acids by the host cell. Methods for the recombinant expression of (mammalian) proteins in a (mammalian) host cell are well known in the art.

As will be clear, a hexavalent single-chain protein hereof finds its use in many therapeutic applications and non-therapeutic applications, e.g., diagnostics or scientific applications. Provided herein is a method for inducing ex vivo or in vivo apoptosis of a target cell, comprising contacting the cell with a hexavalent single-chain protein hereof in an amount that is effective to induce apoptosis. The target cells can be conveniently contacted with the culture medium of a host cell that is used for the recombinant production of the hexavalent single-chain protein. In one embodiment, it can be used for in vitro apoptosis studies, for instance studies directed at the elucidation of molecular pathways involved in MHC class I and class II induced apoptosis. Hexavalent single-chain proteins of the invention may also be used for the detection of (circulating) tumor cells, for the target-cell-specific delivery of cytotoxic compounds or for the delivery of immune-stimulatory molecules.

Preferably, the hexavalent single-chain protein is used for triggering apoptosis of aberrant cells in a subject, more preferably a human subject. For therapeutic applications in humans it is preferred that a hexavalent single-chain protein does not contain amino acid sequences of non-mammalian origin. More preferred are hexavalent single-chain proteins, which only contain human amino acid sequences. Therefore, a therapeutically effective amount of a hexavalent single-chain protein capable of recognizing and binding to a disease-specific epitope can be administered to a patient to stimulate apoptosis of aberrant cells expressing the epitope without affecting the viability of (normal) cells not expressing the disease-specific epitope, e.g., a peptide antigen presented in the context of MHC. It is demonstrated herein that a method of the invention allows for the killing of cells in an antigen-specific, MHC-restricted fashion. In a specific embodiment, the disease-specific epitope is a cancer-epitope, for example, a melanoma-specific epitope. The killing of aberrant (tumor) cells while minimizing or even totally avoiding the death of normal cells will generally improve the therapeutic outcome of a patient following administration of the hexavalent single-chain protein.

Accordingly, there is also provided a hexavalent single-chain protein hereof as medicament. In another aspect, provided is the use of a hexavalent single-chain protein for the manufacture of a medicament for the treatment of cancer. For example, a single-chain protein is advantageously used for the manufacture of a medicament for the treatment of melanoma.

Antibody fragments of human origin can be isolated from large antibody repertoires displayed by phages. One aspect hereof is the use of human antibody phage display libraries for the selection of human Fab fragments specific for MHC class I molecules presenting cancer testis antigenic peptides. Antibody Fab fragments specific for MHC class I, HLA-A0201 molecules presenting a multi-MAGE-A epitope have been selected (essentially as described in R. A. Willemsen et al., *Cytometry A.*, 2008, 73:1093-1099) and shown to bind the relevant antigen only. As these antibody-Fab fragments usually display low affinity a method is provided that allows the generation of relatively high avidity antibody chains able to induce apoptosis in a MHC-restricted peptide specific way. An aspect of the disclosure is the development of a single-chain protein molecule comprising multiple antigen binding motifs to enhance MHC-peptide binding avidity, resulting in cross-linking of the MHC-peptide complexes and induction of apoptosis.

An MHC-p complex-specific polypeptide in a multivalent single-chain monomeric protein form of the invention is, for example, an MHC-restricted antigen-specific TCR-like antibody (Ab) or functional fragment thereof, which is multimerized at the DNA level in order to obtain a single-chain polypeptide construct upon expression.

Human $V_H$ domains usually do not meet the standards for stability and efficient expression that are required by the field. They tend to be unstable and poorly expressed. A process called "camelization" may be used to convert human $V_H$ into more stable antibody fragments.

The human antibody germline region $V_H$-3 displays high homology with antibody $V_H$ fragments of llamas. Llamas have two types of antibodies, those composed of heavy and light chains, and antibodies that only contain heavy chains. These heavy-chain only antibodies bind antigens similar to classical antibodies composed of heavy and light chains. The smallest functional llama antibody binding domain, the $V_{HH}$ domain, also called single domain antibodies (sdAb), has been shown to be expressed well and may bind antigen with high affinity. In addition, it has been shown that some of the characteristics, such as ease of expression and stability, of llama sdAb can be transferred to, e.g., human $V_H$ by replacing a few amino acids in the human $V_H$ for those of llama $V_H$. High avidity antibody molecules can then be generated by ligation of several "camelized" human $V_H$ domains into one single molecule.

Figure 13:
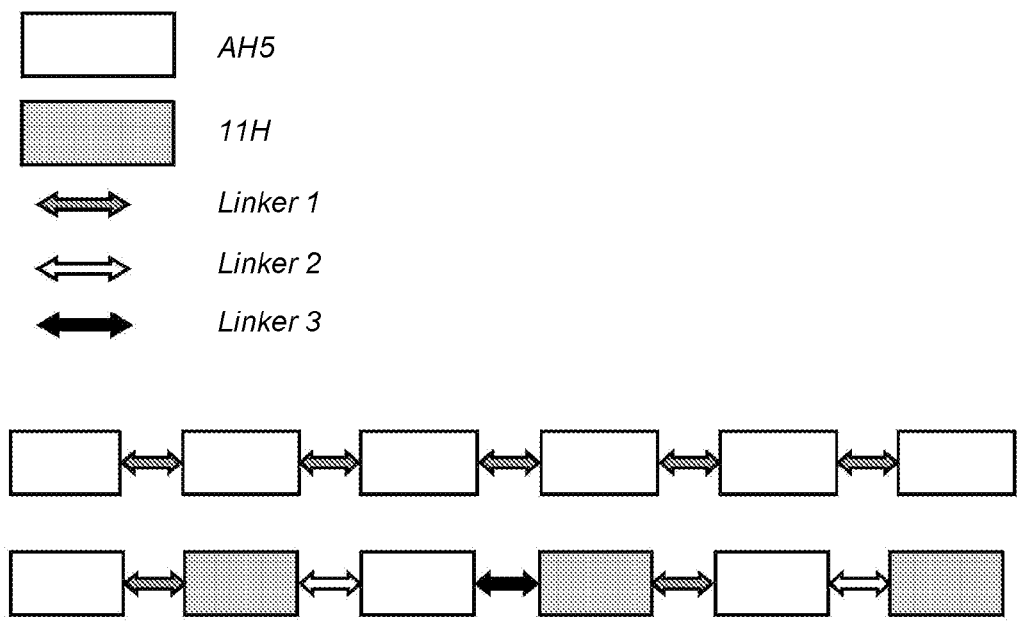
FIG. 13: schematic presentation of possible hexameric proteins. Hexameric proteins may be composed of distinct building blocks, such as: 1) distinct linker sequences and 2) distinct $V_H$ domains. Shown are a number of possible combinations.

Preferred molecules may comprise up to six "camelized" or non-"camelized" human $V_H$ domains interspersed by short linkers providing flexibility between the $V_H$ domains, thus generating six essentially identical binding domains specific for a single epitope (see, for an example, SEQ ID NO:4 and SEQ ID NO:13). For example, a hexavalent mono-specific protein is generated that is specific for the HLA-A0201 restricted multi-MAGE-A epitope within a single polypeptide, referred to as a "single-chain protein" or "single-chain polypeptide" or "monomeric protein" or "monomeric polypeptide." See, for further details, the outlined Examples below. It may be appreciated that this technology allows for the generation of multivalent single-chain proteins that comprise any number of the same or different single domain antibodies. For several reasons (such as, ease of production) repeats are not always the best option. Thus, the invention also contemplates using different binding domains (essentially recognizing the same target) separated by several different linkers, as shown in FIG. 13.

A hexavalent single-chain monomeric protein, according to the invention, comprising six linearly linked human $V_H$ domains is used, for example, to induce apoptosis in cancer cells that express both the MAGE-A genes and HLA-A0201. Noteworthy, specificity for this MHC-peptide complex is provided in this way as cells that do not express HLA-A0201 or that do not express MAGE-A are not killed. See the Examples section for further details. Apoptosis in cancer cells is, for example, detected in vitro by several assays known to the art, including cytotoxicity assays, Tunnel assays and assays detecting active caspases. In animal studies, apoptosis is, for example, revealed by monitoring reduced tumor growth, detection of active caspases or performing a tunnel assay on isolated tumor material.

In literature, it is shown that a single nine amino acid (A.A.) peptide present in MAGE-A2, -A3, -A4, -A6, -A10, and -A12 is presented by HLA-A0201 on tumor cells, and can be recognized by cytotoxic T-lymphocytes.[1] This nine A.A. peptide with sequence Y-L-E-Y-R-Q-V-P-G (SEQ ID NO:7) is almost identical to the HLA-A0201 presented MAGE-A1 peptide Y-L-E-Y-R-Q-V-P-D (SEQ ID NO:9), except for the anchor residue at position 9. Replacement of the anchor residue with Valine results in a 9 A.A. peptide with enhanced binding capacity to HLA-A0201 molecules.

[1] Human and mouse T-lymphocytes recognizing the Y-L-E-Y-R-Q-V-P-V (SEQ ID NO:10) peptide presented by HLA-0201 also recognize the original MAGE-A Y-L-E-Y-R-Q-V-P-G (SEQ ID NO:7) and Y-L-E-Y-R-Q-V-P-D (SEQ ID NO:9) peptides presented on tumors of distinct origin. As diverse tumors may each express at least one MAGE-A gene, targeting of this so-called multi-MAGE-A epitope includes the vast majority of tumors. As an example, MAGE-A expression in human prostate tumor cell lines and in human xenographs was analyzed and shown to be highly diverse, but in each individual sample tested at least one MAGE-A gene was expressed (Table 2), confirming that targeting this multi-MAGE-A epitope serves as an essentially universal HLA-A0201 restricted target for therapy.

Of course, several other multi mage or multi target epitopes may be designed. In principle, the invention contemplates combinations of tumor-specific antigen derived MHC presented epitopes in different HLA restrictions of both MHC-I and MHC-II targeted by multimeric (>=4) binding domains to induce apoptosis in aberrant cell. A number of MHC-peptide combinations that can be targeted (but not limited to) are HLA-A0201/YLEYRQVPG/D (SEQ ID NO:7/9), HLA-CW7/EGDCAPEEK (SEQ ID NO:8), HLA-A24/TFPDLESEK (SEQ ID NO:26) or IMPKAGLLI (SEQ ID NO:27), and HLA-DP4 or HLA-DQ6/KKLLTQH-FVQENYLEY (SEQ ID NO:28).

In one embodiment, human antibody fragments specific for the HLA-A0201 presented multi-MAGE-A epitope Y-L-E-Y-R-Q-V-P-V (SEQ ID NO:10) are identified and isolated from a human phage display library. The selected human antibody fragments are optimized regarding their specificity and avidity, and provide the amino acid sequences used for the design and production of hexavalent single-chain polypeptides specific for efficient binding of the HLA-A0201-MAGE-A Y-L-E-Y-R-Q-V-P-G (SEQ ID NO:7) complex, referred to as hexa-AHS. In another embodiment, hexa-AH5 is produced comprising a C-terminal human antibody Fc domain amino acid sequence, providing hexa-AH5Fc with essentially the same or comparable binding characteristics compared to hexa-AH5. In yet another embodiment, hexa-AH5 is produced comprising a C-terminal human serum albumin (HSA) amino acid sequence, providing hexa-AH5HSA with essentially the same or comparable binding characteristics compared to hexa-AH5.

In one embodiment, the hexa-AH5 and/or its equivalents hexa-H5Fc and/or hexa-H5HSA are used in the production of a pharmaceutical composition. In yet another embodiment, hexa-AH5 construct(s) is/are used for the production of a pharmaceutical composition for the treatment of a disease or a health problem related to the presence of aberrant cells exposing the epitope comprising the HLA-A0201-MAGE-A Y-L-E-Y-R-Q-V-P-G (SEQ ID NO:7) complex for hexa-AH5, hexa-AH5Fc and hexa-AH5HSA. The aberrant cells are, for example, tumor cells. In a further embodiment, hexa-AH5 and/or its equivalents hexa-AH5Fc and/or hexa-AH5HSA is used for the treatment of cancer. In yet another embodiment, hexa-AH5 and/or its equivalent, is used, for example, for the treatment of prostate cancer, breast cancer, multiple myelomas or melanomas.

The disclosure is exemplified by the Examples below.
Abbreviations Used
A.A., amino acid; Ab, antibody; ADA, anti-drug antibodies; AFP, alpha-fetoprotein; APC, antigen presenting cell; β2-M, β2-microglobulin; CDR, complementarity determining region; CEA, carcino-embryonic antigen; CHO, Chinese hamster ovary; CT, cancer testis antigens; CTL, cytotoxic T-lymphocyte; DC, dendritic cell; EBV, Epstein-Barr virus; ELISA, enzyme linked immunosorbent assay; HEK, human embryonic kidney; HLA, human leukocyte antigen; i.v., intravenously; kDa, kilo Dalton; MAGE, melanoma-associated antigen; MHC, major histocompatibility complex; MHC-p, MHC-peptide; PBSM, PBS containing 2% non-fat dry milk; sc-Fv, single-chain variable fragment; $V_{HH}$ or sdAb, single domain antibodies; TCR, T-cell receptor; VH, Vh or $V_H$, variable amino acid sequence of an antibody heavy domain.

EXAMPLES

Example 1

Selection of Human Antibody Fragments Specific for HLA-A0201/Multi-MAGE-A

To obtain human antibody fragments specific for the HLA-A0201 presented multi-MAGE-A epitope Y-L-E-Y-R-Q-V-P-G (SEQ ID NO:5) a Human Fab phage display library was constructed according to the procedure previously described by de Haard et al.[2] and used for selections essentially as described by Chames et al.[3] Human Fab phages ($10^{13}$ colony-forming units) were first pre-incubated for 1 hour at room temperature in PBS containing 2% non-fat dry milk (PBSM). In parallel, 200 µl Streptavidin-coated beads (Dynal) were equilibrated for 1 hour in PBSM. For subsequent rounds, 100 µl beads were used. To deplete for pan-MHC binders, each selection round, 200 nM of biotinylated MHC class I-peptide (MHC-p) complexes containing an irrelevant peptide (Sanquin, the Netherlands) were added to the phages and incubated for 30 minutes under rotation. Equilibrated beads were added, and the mixture was incubated for 15 minutes under rotation. Beads were drawn to the side of the tube using magnetic force. To the depleted phage fraction, subsequently decreasing amounts of biotinylated MHC-p complexes (200 nM for the first round, and 20 nM for the second and third round) were added and incubated for 1 hour at room temperature, with continuous rotation. Simultaneously, a pan-MHC class I binding soluble Fab (D3) was added to the phage-MHC-p complex mixture (50, 10, and 5 µg for rounds 1-3, respectively). Equilibrated streptavidin-coated beads were added, and the mixture was incubated for 15 minutes under rotation. Phages were selected by magnetic force. Non-bound phages were removed by five washing steps with PBSM, five steps with PBS containing 0.1% TWEEN®, and five steps with PBS. Phages were eluted from the beads by 10 minutes incubation with 500 µl freshly prepared tri-ethylamine (100 mM). The pH of the solution was neutralized by the addition of 500 µl 1 M Tris (pH 7.5). The eluted phages were incubated with logarithmic growing *E. Coli* TG1 cells ($OD_{600nm}$ of 0.5) for 30 minutes at 37° C. Bacteria were grown overnight on 2× TYAG plates. The next day, colonies were harvested, and a 10 µl inoculum was used in 50 ml 2× TYAG. Cells were grown until an $OD_{600nm}$ of 0.5, and 5 ml of this suspension was infected with M13k07 helper phage ($5\times10^{11}$ colony-forming units). After 30 minutes incubation at 37° C., the cells were centrifuged, resuspended in 25 ml 2× TYAK, and grown overnight at 30° C. Phages were collected from the culture supernatant, as described previously, and were used for the next round panning. After three selection rounds a 261-fold enrichment was obtained, and 46 out of 282 analyzed clones were shown to be specific for the HLA-A2-multi-MAGE-A complex (FIG. 1). ELISA using the HLA-A0201/multi-MAGE-A complexes as well as HLA-A0201 complexes with a peptide derived from JC virus was used to determine the specificity of the selected Fab.

Figure 2:
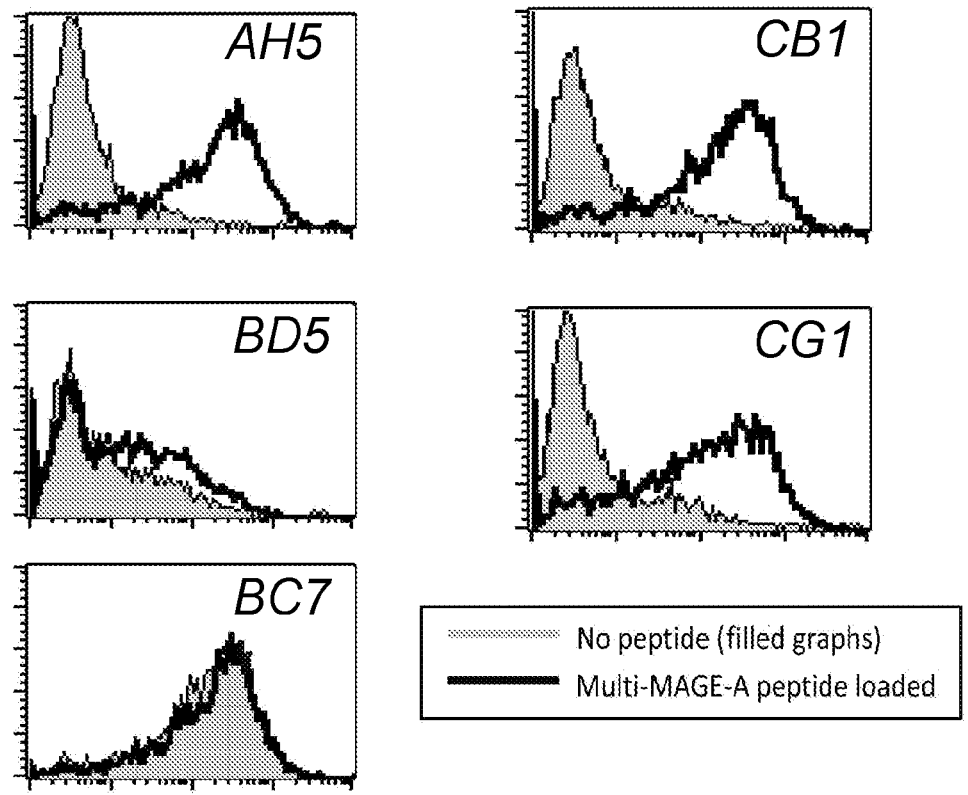
FIG. 2: Phages AH5, CB1 and CG1 specifically bind cells presenting the multi-MAGE-A peptide. Phages AH5, CB1, CG1, BD5 and BC7 that had shown specific binding in ELISA using the relevant HLA-A201/multi-MAGE-A complex and an irrelevant HLA-A201 complex loaded with a JCV peptide were analyzed for their capacity to bind cells presenting the multi-MAGE-A peptide in HLA-A0201 molecules. To this end, human B-LCL (BSM) were loaded with multi-MAGE-A peptide (10 µg in 100 µl PBS) for 30 minutes at 37° C., followed by incubation with the Fab phages AH5, CB1, CG1, BD5 and BC7 and analyzed by flow-cytometry using anti-phage antibodies and a fluorescently labeled secondary antibody.

1.2 Human Fab Specific for the HLA-A0201/Multi-MAGE-A Epitope Bind Antigen-Positive Cells Selected Fab phages were then analyzed for their capacity to bind HLA-A0201-positive EBV-transformed B-LCL loaded with the multi-MAGE-A peptide Y-L-E-Y-R-Q-V-P-V (SEQ ID NO:10). The B-LCL line BSM ($0.5\times10^6$) was loaded with multi-MAGE-A peptide (10 µg in 100 µl PBS) for 30 minutes at 37° C., followed by incubation with the Fab phages AH5, CB1, CG1, BD5 and BC7 and analyzed by flow-cytometry. As shown in FIG. 2, Fab AH5, CB1 and CG1, specifically bound to the peptide loaded cells only, whereas Fab BD5 and BC7 displayed non-specific binding to BSM that was not loaded with the multi-MAGE-A peptide. No binding was observed by AH5, CB1 and CG1 to non-peptide loaded cells.

Phages presenting AH5, CB1 and CG1, as well as the HLA-A0101/MAGE-A1-specific Fab phage G8[4] were then used to stain tumor cell lines of distinct histologic origin. To this end prostate cancer cells (LNCaP), multiple myeloma cells (MDN), melanoma cells (MZ2-MEL43 and G43), and breast cancer cells (MDA-MB157) were stained and analyzed by flow cytometry (FIG. 3). The Fab AH5 specifically bound multiple myeloma cells MDN, and not the HLA-A0201-negative melanoma and breast cancer cells. Both CB1 and CG1 displayed non-specific binding on the melanoma cell line G43. The positive control Fab G8 demonstrated binding to all cell lines tested.

1.3 Fab AH5 Binds HLA-A0201/Multi-MAGE-A Complexes Only

Figure 4:
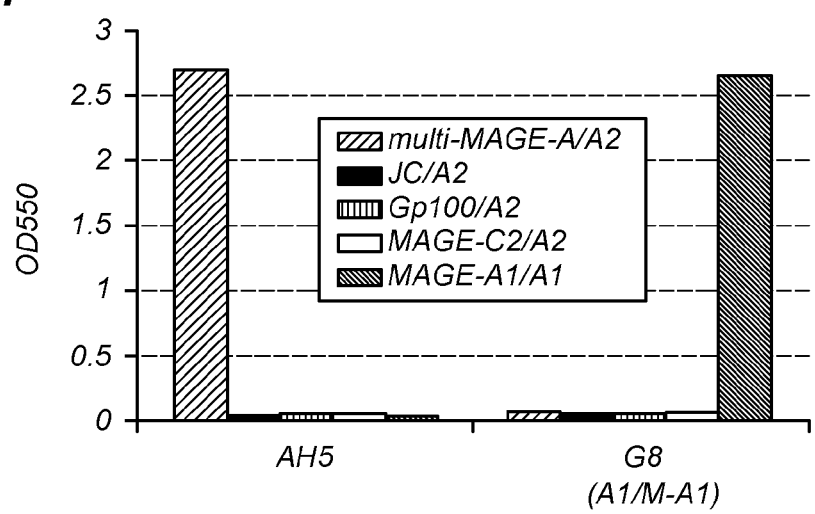
FIG. 4: Phage AH5 specifically binds HLA-A0201/multiMAGE-A complexes only. To determine specificity of the phage AH5 an ELISA was performed using relevant and irrelevant peptide/MHC complexes. HLA-A0201 with multi-MAGE-A, gp100, JCV and MAGE-C2 peptides, as well as HLA-A1 with MAGE-A1 peptide were coated on streptavidin 96-well plates and incubated with phage AH5.

ELISA using multiple peptide/MHC complexes then confirmed the specificity of Fab-AH5. To this end HLA-A0201 complexes presenting peptides multi-MAGE-A, gp100, JCV and MAGE-C2, as well as a HLA-A1/MAGE-A1 complex were immobilized on 96 well plates and incubated with phages displaying Fab AH5 and control Fab G8. As shown in FIG. 4, AH5 only binds HLA-A0201/multi-MAGE-A and not the irrelevant complexes HLA-A0201/gp100, HLA-A0201/MAGE-C2, HLA-A0201/JCV and HLA-A0101/MAGE-A1. The positive control Fab G8 only binds to its relevant target HLA-A0101/MAGE-A1.

Example 2

Production of Hexameric Proteins Comprising Camelized Single Domains AH5 VH Domains 2.1 Design of Genes for Production of Hexameric AH5 VH Proteins Human antibody germline gene VH3 demonstrates high homology to llama single domains VHH. Exchange of amino acids 44, 45 and 47 in the human VH3 genes by amino acids present in llama VHH at these positions has shown to enhance stability and expression of the human VH3 genes.[5] The AH5 VH demonstrates a low homology to germline gene VH3-33*01 (71% as determined by IMGT homology search) however, its expression and stability might benefit from the exchange of amino acids 44, 45 and 47 by llama VHH amino acids, a process called camelization. In addition a gene was compiled that upon expression would comprise six AH5 VH domains. To this end, a gene called hexa-AH5 was designed comprising the pelB secretion signal, which was operatively linked to six codon-optimized, camelized AH5 VH domains with GSTSGS linkers between each AH5 VH domain (see hexa-AH5, see SEQ ID NO:1 for the DNA sequence and SEQ ID NO:4 for the amino acid sequence). This gene was synthesized by "Geneart" (Regensburg, Germany) and cloned into the pStaby 1.2 vector (Delphi genetics, Belgium) for expression in E coli.

2.2 Production and Purification of Hexameric AH5 VH Protein

Figure 5:
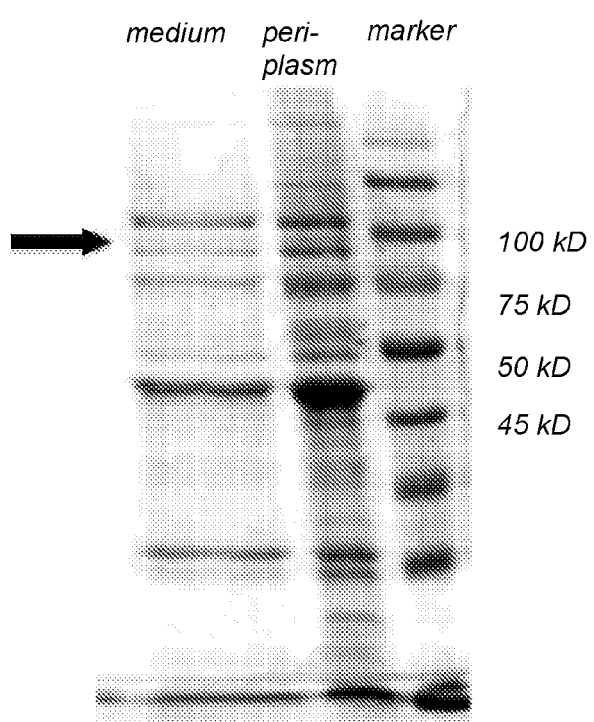
FIG. 5: Hexa-AH5 is expressed by bacteria. Expression of the Hexa-AH5 gene in pStaby 1.2 was induced after addition of IPTG to SE-1 bacteria. Bacteria were grown in TYAG medium at 30° C. until OD600=0.8. At that time, medium was replaced with TY medium supplemented with IPTG, and bacteria allowed to grow for four hours. Medium and periplasm were collected and analyzed by 10% SDS-PAGE.

For expression of hexameric AH5 VH proteins (hexa-AH5, see SEQ ID NO:1 for the DNA sequence and SEQ ID NO:4 for the amino acid sequence) the pStaby-Hexa-AH5 vectors were introduced via electroporation into SE1 bacteria. Positive clones were grown in the presence of 2% glucose at 30° C. until $OD_{600}$=0.8. Bacterial TYAG medium was then replaced with TY medium containing 1 mM IPTG to induce expression. After overnight culture at 30° C. bacteria and medium were harvested. The periplasm fraction was collected after incubation of bacteria with PBS/EDTA/NaCl for 30 minutes on ice. Protein expression was then analyzed by SDS-PAGE. As shown in FIG. 5, Hexa-AH5 protein was secreted into the medium and was present in the bacterial periplasm.

Hexameric AH5 VH proteins were isolated from media and bacteria using Ni-affinity purification. To this end, medium was incubated with Ni-coupled Sepharose-beads and incubated overnight, while stirring gently. To obtain intracellular proteins bacteria were lysed and cellular debris removed by centrifugation. After overnight dialysis with PBS Hexameric AH5 VH proteins were purified with Ni-Sepharose. Purity of the Hexameric AH5 VH proteins was checked by SDS-PAGE and protein concentration determined by BCA protein assay (Pierce).

Example 3

Hexameric AH5 VH Proteins Induce Apoptosis in Diverse Tumor Cells

Cross-linking of MHC class I molecules by pan-MHC class-I and β2M-specific antibodies results in the induction of apoptosis.[6] This process was shown to be caspase-9 dependent and results in the eradication of MHC class I-positive tumor cells in vitro and in vivo. The induction of apoptosis by pan-MHC class I antibodies and anti-β2M-specific antibodies is not specific for tumors expressing tumor-specific antigens. In contrast, cross-linking of peptide/MHC molecules through the interaction of molecules that resemble T-cell receptors binding to specific peptide/MHC complexes will result in tumor-specific apoptosis induction. Efficient cross-linking will depend on the number of peptide/MHC complexes that are simultaneously bound by the therapeutic molecule.

3.1 Hexameric AH5 Protein Kills Diverse Tumor Cells

Figure 6:
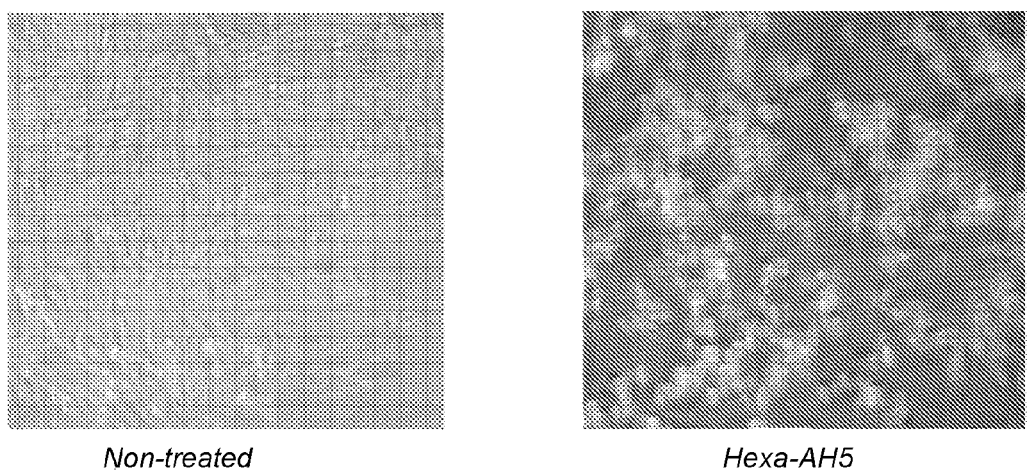
FIG. 6: Microscopic analysis of Hexa-AH5-treated Daju cells reveals apoptosis. Daju cells cultured in DMEM medium supplemented with pen/strep, glutamine and non-essential amino acids were treated with heza-AH5 protein (10 μg/ml total) for four hours and inspected by microscopy for signs of apoptosis.

The hexameric AH5-VH proteins were analyzed for their capacity to induce apoptosis by incubation with diverse tumor cells, known to express both HLA-A0201 and MAGE-A genes. The cell-lines Daju, Mel 624 (melanoma), PC346C (prostate cancer), as well as MAGE-A-negative cells (911 and HEK293T) were incubated with 10 μg/ml Hexa-AH5 protein (in DMEM medium, supplemented with pen/strep, Glutamine and non-essential amino acids). Four hours later, cells were visually inspected for classical signs of apoptosis, such as detachment of the cells from tissue culture plates and membrane blebbing. As shown in FIG. 6, Daju cells indeed detach from the tissue culture plates only after incubation with the Hexa-AH5 protein. This was also seen for the Mel 624 and PC346C cells. When incubation was extended to overnight, Daju, Mel624 and PC346C cells were disintegrated and notably absent in the treated cultures. Cells that were not treated with the hexa-AH5 protein were not affected, as well as cells that do not express HLA-A0201 (HEK293T) and MAGE-A genes (911 and HEK293T).

3.2 Hexameric AH5 Protein Induces Active Caspase-3

A classical intra-cellular hallmark for apoptosis is the presence of active caspase-3. To determine whether or not the Hexameric AH5 proteins induce active caspase-3, Daju cells were incubated with 10 μg/ml Hexa-AH5 protein. After four hours FAM-DEVD-FMK (SEQ ID NO:25), a fluorescently labeled inhibitor for caspase-3/7 was added to the tissue culture medium. This substrate can pass the cell-membrane and only when active caspase-3 is present, a bright fluorescent signal will be detected by, e.g., fluorescent microscopy.

Figure 7:
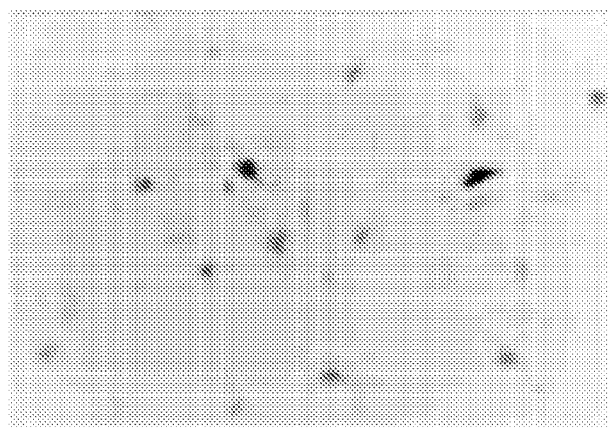
FIG. 7: Treatment with Hexa-AH5 induces active caspase-3. Daju cells were treated with 10 μg/ml Hexa-AH5 protein for four hours. Next, a caspase-3 inhibitor was added (FAM-DEVD-FMK) and 1 hour later cells were analyzed by fluorescence microscopy.

As shown in FIG. 7, Daju cells treated with Hexa-AH5 protein are emitting a fluorescence signal demonstrating the presence of active caspase-3. Cells that were not treated did not show fluorescence, demonstrating the specificity of the caspase-3 inhibitor.

Example 4

Hexameric AH5 Protein Induces Apoptosis in a Transplantable Human Tumor Model

To demonstrate apoptotic activity of the Hexa-AH5 proteins in three-dimensional human tumors, an orthotopic prostate cancer model was used. To this end, human PC346C prostate cancer cells were injected into the prostate of male NOD-SCID mice and allowed to grow until tumors were detectable by ultrasound guided inspection.

4.1 Intra-Tumoral Injection of Hexa-AH5 Results Induces Apoptosis

The human PC346C prostate tumors in NOD-SCID mice were injected once directly with 10 μg Hexa-AH5 protein (in 20 μl total volume). The next day, tumors were removed, fixed and paraffin embedded. Slides were prepared from the paraffin-embedded tumors and stained with the Tunnel Universal Apoptosis Detection Kit (Genescript), an assay that detects fragmented DNA, a classical marker of apoptosis. In brief, slides were heated for 30 minutes at 60° C., washed three times with PBS, and incubated for one hour with proteinase K solution. Slides were then incubated with blocking solution (3% $H_2O_2$ in methanol) for 10 minutes, washed with PBS and incubated for one hour at 37° C. with Tunnel reaction mixture (equilibrium buffer, Biotin-11-dUTP, and TdT). After three washes slides were incubated with Streptavidin-HRP solution for 30 minutes at 37° C., and finally incubated with DAB-substrate (DAB-buffer, $H_2O_2$ in PBS).

Figure 8:
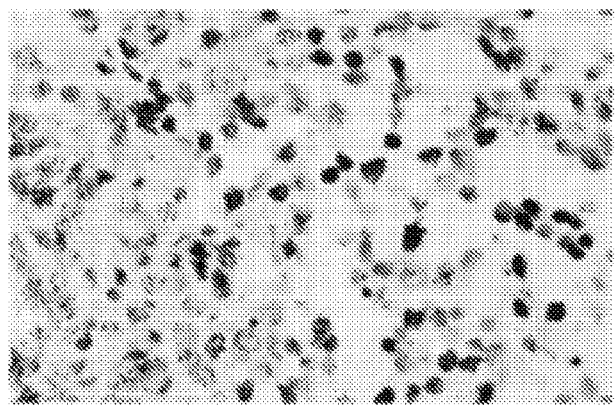
FIG. 8: Intratumoral injection of Hexa-AH5 induces apoptosis in a transplantable human tumor model. The human prostate tumor cell line PC346C was injected into the prostate of NOD-Scid mice and allowed to grow until visible by ultrasound inspection. The mice then received an intratumoral injection of Hexa-AH5 (10 μg total in 20 μl volume) or PBS as control. The next day, the mice were sacrificed, tumors removed and paraffin embedded. Tumor slices were stained for fragmented DNA and analyzed by microscopy. Results show large areas of apoptotic cells (stained dark) only after treatment with Hexa-AH5. No signs of apoptosis were detected in PBS-treated mice.

Microscopic analysis of tumor material treated with Hexa-AH5 demonstrates large areas of apoptotic cells (see FIG. 8). Untreated tumors do not show any signs of DNA damage 4.2 Intravenous Injection of Hexa-AH5 Induces Apoptosis in Orthotopic Prostate Cancer Cells 4.2.1 Prostate Tumor Cells Demonstrate Nicked DNA after i.v. Injection with Hexa-AH5

In a next experiment NOD-scid mice with the orthotopic human PC346C prostate tumor were injected once via tail vain with 25 μg Hexa-AH5 (in 150 μl total volume). The next day, tumors were removed, paraffin embedded and tumor slides stained for Nicked DNA with the Tunnel assay.

Figure 9:
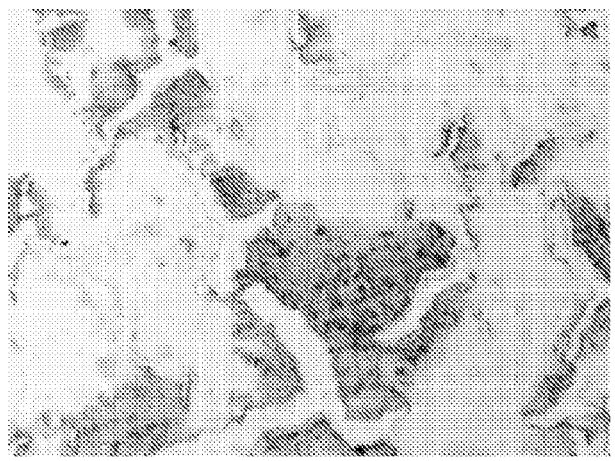
FIG. 9: Intravenous injection of Hexa-AH5 results in apoptotic prostate tumor cells in the orthotopic mouse tumor model. NOD-scid mice with orthotopic PC346C prostate tumor were injected once with 25 μg Hexa-AH5 (in 100 μl total volume). The next day, mice were sacrificed and tumors removed. Paraffin-embedded tumor slices were stained for fragmented DNA and analyzed by microscopy. Results show large areas of apoptotic cells in treated mice only.

As shown in FIG. 9, large areas of apoptotic cells are present in Hexa-AH5-treated mice, whereas non-treated mice did not show any signs of apoptosis.

4.2.2 Prostate Tumor Cells Demonstrate Active Caspase after i.v. Injection with Hexa-AH5

NOD-scid mice with the orthotopic PC346C tumor were injected once via tail vain with 25 µg Hexa-AH5 (in 150 µl total volume). The next day, these mice received an injection with FLIVO (Immunohistochemistry Ltd.), a fluorescently labeled caspase inhibitor. This inhibitor was allowed to circulate and pass cellular membranes for one hour. Tumors were then removed, fixed and paraffin embedded.

Figure 10:
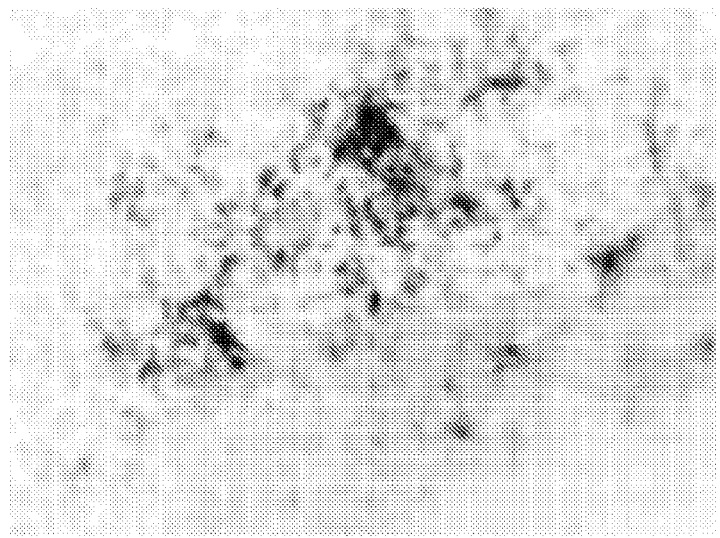
FIG. 10: Intravenous treatment with Hexa-AH5 of mice with orthotopic prostate cancer results in activation of caspases. NOD-scid mice with orthotopic PC346C prostate tumor were injected once with 25 μg Hexa-AH5 (in 100 μl total volume). The next day, mice received an intravenous injection with a universal caspase inhibitor (FLIVO), which was allowed to circulate for one hour. Mice were then sacrificed and tumors removed. Paraffin-embedded tumor slices were analyzed by fluorescence microscopy, which revealed active caspase in Hexa-AH5-treated mice only.

Analysis of Hexa-AH5-treated tumors by fluorescence microscopy demonstrated the presence of numerous cells that stained positive for the caspase substrate (see FIG. 10). No fluorescently labeled cells were detected in untreated mice.

Example 5

Construction of Hexa-AH5 Genes to Improve Circulation and Tumor Penetration

The pharmacokinetic properties of therapeutic proteins, e.g., their distribution, metabolism and excretion are dependent on factors, such as shape, charge and size. Most small plasma molecules (MW<50-60 kDa) possess very short half-life, whereas larger plasma proteins, such as human serum albumin (HSA) and immunoglobulins (Ig) have very long half-lives (19 days for HSA, 1-4 weeks for Ig). Indeed, addition of IgG-Fc or Human serum albumin has shown to extend circulation time, tumor penetration and antitumor effects when linked to therapeutic proteins.

5.1 Construction of Hexameric AH5 with IgG1-Fc and Human Serum Albumin

The Hexameric AH5 construct was linked to the IgG1-Fc region or to human serum albumin, codon optimized for expression in eukaryotic cells and cloned into the pcDNA-3.1+ vector (Geneart, Regensburg, Germany) (see DNA sequence with SEQ ID NO:2 and amino acid sequence with SEQ ID NO:5 for hexa-AH5Fc, and see DNA sequence with SEQ ID NO:3 and amino acid sequence with SEQ ID NO:6 for hexa-AH5HSA, respectively).

5.2 Hexameric AH5-Fc and AH5-HSA Induce Active Caspase-3

Figure 11A:
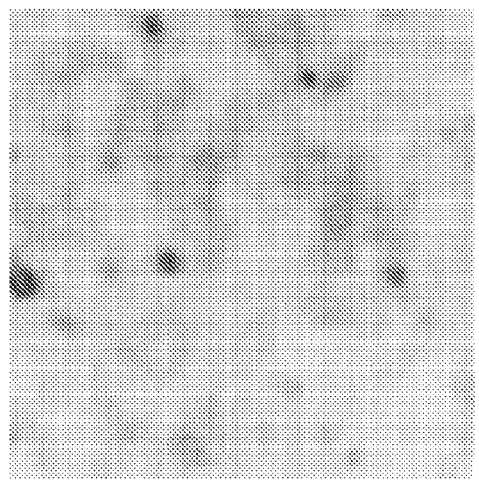
FIG. 11: Treatment with Hexa AH5-Fc and AH5-HSA induces active caspase-3. Melanoma 624 cells incubated for 24 hours with supernatant obtained from 293T cells transfected with the pcDNA-3.1/Hexa AH5-Fc (A) or /Hexa AH5-HSA (B) constructs demonstrate presence of active caspase-3. Active caspase-3 in melanoma 624 cells was detected by fluorescence microscopy 4 hours after incubation with FAM-DEVD-FMK (SEQ ID NO:25).
Figure 11B:
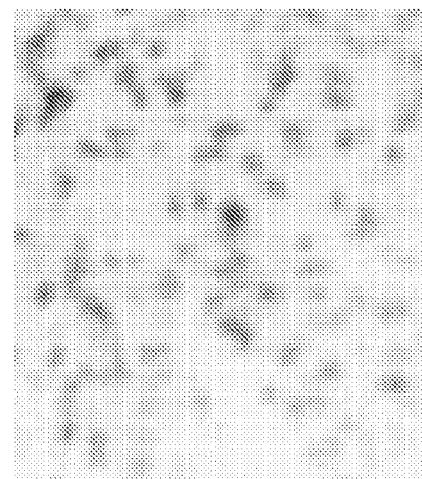

The hexameric AH5-FC and AH5-HSA constructs, cloned into pcDNA-3.1+, were expressed in 293T cells. Supernatant obtained four days after transfection was used to induce apoptosis in melanoma 624 cells known to express HLA-A0201 and MAGE-A genes. To this end, melanoma 624 cells were seeded in 24-well plates ($0.25 \times 10^6$ cells/well) and allowed to attach overnight. The next day, medium was replaced with medium obtained from transfected 293T cells. Results showed positive caspase-3 staining for 624 melanoma cells treated with both hexa-AH5-Fc and Hexa-AH5-HSA. No staining was observed for 624 cells incubated with plain medium or HLA-A0201 positive, MAGE-A-negative 911 cells (FIG. 11).

5.3 Extended Survival of Mice and Delayed Tumor Growth of Mice Treated with Hexameric AH5

Mice inoculated with melanoma cell line Daju (HLA-A0201/MAGE-A positive) were treated with intravenous injections of hexameric AH5 protein (2.5 ug/2 times/week). Shown are 1) tumor free mice, and 2) tumor growth (FIG. 12)

5.4 Enhanced Induction of Apoptosis by Dimeric Hexameric AH5CH1 and 11HCH1

For expression in eukaryotic cells the AH5CH1 and 11HCH1 sequences were introduced into the pMSec SUMOSTAR vector (Hexameric AH5CH1 and 11HCH1 were produced in supernatant of 293T cells after transfection with CaPO4. One hour after incubation of Daju and MEL624 melanoma cells with 293T supernatant (1:1 diluted in DMEM, 5% FCS) membrane blebbing and detachment of cells were observed 5.5 Improved Expression of Hexameric AH5 at 25° C.

Figure 14A:
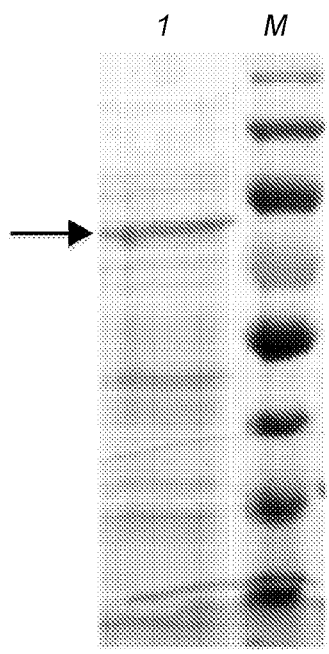
FIG. 14: Expression of Hexameric AH5 at 25° C. SE-1 bacteria containing the Hexameric AH5 construct were grown and induced at 25° C. FIG. A, instant blue staining of SDS-PAGE gel: lane 1-periplasm of induced SE-1 pStaby 1.2-Hexa-AH5, lane 2: protein marker (M). FIG. B, western blot with anti-cMyc antibody: lane 1: Hexa-AH5, lane 2 protein marker (M).
Figure 14B:
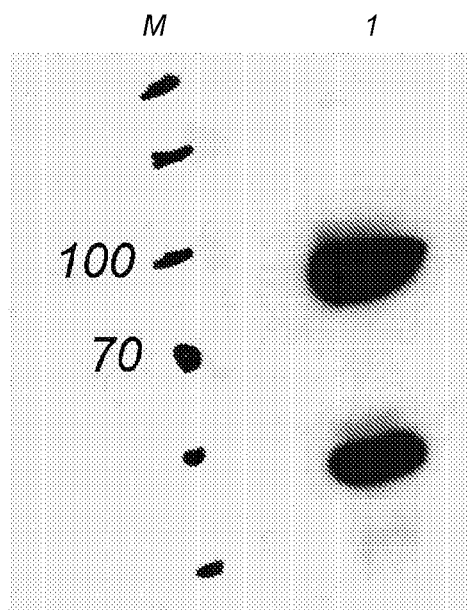

Expression of Hexameric AH5 in SE1 at 30° C. or 37° C. in shaking flasks was shown to result in many unwanted smaller products. Lowering the temperature during growth and production to 25° C. resulted in a marked improvement of production. Less, to no side products were obtained as well as a higher yield of the protein (FIGS. 14A and 14B).

TABLE 1

Examples for the frequency of MAGE-A expression by human cancers

Table 1: Examples for the frequency of MAGE-A expression by human cancers Frequency of expression (%)

| cancer | MAGE-A1 | MAGE-A2 | MAGE-A3 | MAGE-A4 | MAGE-A6 | MAGE-A10 | MAGE-A11 |
|---|---|---|---|---|---|---|---|
| Melanoma | 16 | E | 36 | E | 64 | E | 74 |
| Head and neck | 25 | 42 | 33 | 8 | N | N | N |
| Bladder | 21 | 30 | 35 | 33 | 15 | N | 9 |
| Breast | 6 | 19 | 10 | 13 | 5 | N | N |
| Colorectal | N | 5 | 5 | N | 5 | N | N |
| Lung | 21 | 30 | 46 | 11 | 8 | N | N |
| Gastric | 30 | 22 | 57 | N | N | N | N |
| Ovarian | 55 | 32 | 20 | E | 20 | N | N |
| osteosarcoma | 62 | 75 | 62 | 12 | 62 | N | N |
| hepatocarcinoma | 68 | 30 | 68 | N | 30 | 30 | 30 |
| Renal cell carcinoma | 22 | 16 | 76 | 30 | N | N | N |

Table 1B. Expression analysis of MAGE-A1-A6 genes detected by nested RT-PCR with common primers in squamous cell carcinoma of the head and neck.

| Primary site | % of positive expression |
|---|---|
| Larynx | 72.7% (8/11) |
| Hypopharynx | 100% (2/2) |
| Base of tongue | 50% (1/2) |

TABLE 1-continued

Examples for the frequency of MAGE-A expression by human cancers

| | |
|---|---|
| Tonsil | 100% (2/2) |
| Total (n = 17) | 76.5% (13/17) |

E, expressed but the frequency is not known; N, expression by tumors has never been determined or observed
Adapted from: ANTICANCER RESEARCH 26: 1513-1518 (2006)

TABLE 2

MAGE-A expression in human prostate cancer cell lines and prostate cancer xenografts.
Table 2: MAGE-A expression in human prostate cancer cell lines and prostate cancer xenografts.

| Cell line/ Xenograft | MAGE- | | | | | | | | | | | |
|---|---|---|---|---|---|---|---|---|---|---|---|---|
| | A1 | A2 | A3 | A4 | A5 | A6 | A7 | A8 | A9 | A10 | A11 | A12 |
| LNCaP | + | ++ | ++ | | | ++ | + | | | | | |
| PC346C | + | ++ | ++ | + | | ++ | + | | | + | ++ | |
| OVCAR | | | + | + | | + | | | | + | | |
| JON | | ++ | ++ | | | ++ | | | | + | + | |
| PNT 2 | | | + | + | | + | | | | + | + | |
| C2 | | | | | | | | | | | | |
| SD48 | | | | + | | + | | | | + | + | |
| PC-3 | | | | | | + | | | | + | + | |
| PC 374 | | + | | | | | | | | | | |
| PC 346p | + | ++ | ++ | | | ++ | | | + | | ++ | + |
| PC 82 | | | + | + | | | | | | | | |
| PC 133 | ++ | + | | | | | | + | | | | |
| PC 135 | + | | | | | | | | | | | |
| PC 295 | + | | | | | | | | | | | |
| PC 324 | | | + | | | + | | + | | | | |
| PC 310 | + | ++ | | + | | ++ | | | | | | + |
| PC 339 | | ++ | ++ | | + | ++ | + | + | | | | + |

Expression of the MAGE-A1, A2, A3, A4, A5, A6, A7, A8, A9, A10, A11 and A12 genes in diverse prostate tumor cell lines and prostate xenografts was analyzed by RT-PCR. Shown are expression levels in individual samples tested. Blank= no expression, + = low expression, ++ = high expression.
All cell lines/xenografts express at least one MAGE-A gene.

REFERENCES (1) Stephanie Graff-Dubois, Olivier Faure, David-Alexandre Gross, Pedro Alves, Antonio Scardino, Salem Chouaib, Francois A. Lemonnier and Kostas Kosmatopoulos. Generation of CTL Recognizing an HLA-A*0201-Restricted Epitope Shared by MAGE-A1, -A2, -A3, -A4, -A6, -A10, and -A12 Tumor Antigens: Implication in a Broad-Spectrum Tumor Immunotherapy. *The Journal of Immunology,* 2002, 169:575-580.

(2) Hans J. de Haard, Nicole van Neer, Anneke Reurs, Simon E. Hufton, Rob C. Roovers, Paula Henderikx, Adriaan P. de Bruine, Jan-Willem Arends, and Hennie R. Hoogenboom. A Large Non-immunized Human Fab Fragment Phage Library That Permits Rapid Isolation and Kinetic Analysis of High Affinity Antibodies. *The Journal of Biological Chemistry,* 1999, 274:18218-18230.

(3) P. Chames, H. R. Hoogenboom, and P. Henderikx. Selection of antigens against biotinylated antigens. In Antibody phage display, methods and protocols, Edited by P. M. O'Brien and R. Aitken. *Methods in Molecular Biology* 2002, 178:147-159.

(4) Patrick Chames, Simon E. Hufton, Pierre G. Coulie, Barbara Uchanska-Ziegler, Hennie R. Hoogenboom. Direct selection of a human antibody fragment directed against the tumor T-cell epitope HLA-A1-MAGE-A1 from a nonimmunized phage-Fab library. *PNAS,* 2000. 97:7969-7974.

(5) Lutz Riechmann, Serge Muyldermans. Single domain antibodies: comparison of camel VH and camelized human VH domains. *Journal of Immunological Methods* 1999, 231:25-38.

(6) Jing Yang, PhD and Qing Yi. Killing Tumor Cells Through Their Surface b2-Microglobulin or MajorHistocompatibility Complex Class I Molecules. *Cancer* 2010. 116:1638-1645.

What is claimed is:

1. A polypeptide comprising Hexa-AH5: (SEQ ID NO:4), or Hexa-11HCH1: (SEQ ID NO:13), or Hexa-11HAH5: (SEQ ID NO:17).

2. The polypeptide of claim 1, wherein the linker amino acid sequences allow for protein folding.

3. The polypeptide of claim 1, which comprises SEQ ID NO:4.

4. The polypeptide of claim 1, which comprises SEQ ID NO: 13.

5. The polypeptide of claim 1, which comprises SEQ ID NO: 17.

6. A pharmaceutical composition comprising: the polypeptide of claim 1, and a suitable diluent and/or excipient.

7. The pharmaceutical composition according to claim 6, further comprising a cytostatic and/or tumoricidal agent.

8. A conjugate of a polypeptide of claim 1, and a cytostatic or tumoricidal agent.

9. A method for producing the polypeptide of claim 1, the method comprising: culturing a host cell comprising a polynucleotide encoding the polypeptide, allowing for expression of the polynucleotide, and harvesting the polypeptide.

* * * * *

SEQUENCE LISTING

```
<160> NUMBER OF SEQ ID NOS: 28

<210> SEQ ID NO 1
<211> LENGTH: 2226
<212> TYPE: DNA
<213> ORGANISM: Artificial
<220> FEATURE:
```

<223> OTHER INFORMATION: DNA sequence Hexa-AH5

<400> SEQUENCE: 1

```
cagctgcagc tgcaagaaag cggtggtggt gttgttcagc ctggtcgtag cctgcgtctg      60
agctgtgcag caagcggttt tacctttagc agctatggta tgcattgggt tcgtcaggca     120
ccgggtaagg aacgtgaagg tgttgcagtt attagctatg atggcagcaa caaatattat     180
gccgatagcg ttaaaggtcg ctttaccatt agccgtgata tagcaaaaa caccctgtat      240
ctgcagatga atagcctgcg tgcagaagat accgcagttt attattgtgc cggtggtagc     300
tattatgttc cggattattg gggtcagggc accctggtta ccgttagcag cggtagcacc     360
agcggtagca tggcccagct gcaattacaa gaatcaggtg gtggcgtggt gcagccaggt     420
cgttcactgc gtctgtcatg tgcagcatca ggctttacct tcagttcata cggcatgcac     480
tgggtgcgcc aagctccagg caaagaacgc gaaggcgtgg ccgttatttc atacgatggc     540
tccaataaat actatgcgga ttcagtgaaa ggccgtttta ccatttcacg cgataacagt     600
aaaaacacct tatacctgca aatgaattca ctgcgtgccg aggatacagc cgtgtattac     660
tgtgcgggtg gttcatatta cgtgcctgat tattggggac aaggtacact ggtgacagtt     720
agcagtggta gtacctcagg ttcaatggcc cagttacaac tgcaagaatc tggcggtggt     780
gttgtgcaac cgggtcgctc tctgcgtctg agttgcgctg catcaggttt tacattttca     840
agctacgaa tgcactgggt tagacaggct cccggtaagg aaagagaagg cgttgcggtt      900
atcagttatg acggtagcaa taagtattat gcggactctg ttaagggtcg ttttacaatt     960
tctcgggaca atagcaagaa tacactgtac ttacagatga actctctgag agcagaagat    1020
acagccgtat actattgcgc aggcggtagt tattatgtgc ctgactactg gggccaggga    1080
acgctggtga ccgtgagtag cggttcaacc agcggttcaa tggcgcaact gcaacttcaa    1140
gagtctggtg gcggtgtggt acagcctggc cgttctctgc gtttaagctg cgcagcctct    1200
ggttttacgt tttcatctta tggaatgcat tgggtacgcc aagcccctgg aaaagaacgt    1260
gagggcgtag cagtgatctc ttatgatggt tcgaacaaat attacgcgga ctccgtgaaa    1320
ggacgcttta caatctctcg tgataactca aaaaatacgc tgtatcttca aatgaactcc    1380
ttacgtgcgg aagatactgc ggtctattac tgcgctggcg gttcttacta tgtaccagat    1440
tactggggac aggggacctt agttacagtt agctcaggta gcaccagtgg ttctatggct    1500
caattacagt tacaagaaag tggcggtggc gtggtccaac ctggccgtag tctgcgcctg    1560
tcttgcgcag cgagcggctt tacattttct agttatggca tgcattgggt gagacaagct    1620
ccgggggaaag agcgcgaagg ggttgcggtg atttcttatg acggcagtaa taaatactac    1680
gcagatagtg tgaaaggtcg tttcacaatt agtcgcgata ctccaaaaa cacattatat     1740
ttgcagatga acagtttgcg tgcggaggac acggctgtat attattgtgc aggggggttcc    1800
tactatgtgc ccgactactg gggtcaaggg accttagtga ccgtttcaag cggtagtacc    1860
tctggtagta tggctcaact tcagctgcaa gagtcaggcg gaggcgttgt ccagcctgga    1920
cgctcactgc gcttaagttg tgcagccagt ggctttacgt ttagctctta cgggatgcat    1980
tgggtccggc aggcgcctgg gaaggaacgc gaaggtgtag ctgtgattag ttacgatggc    2040
agtaataagt attacgccga ttcagtaaaa ggtcgcttca cgatttcgcg tgataattct    2100
aagaataccc tttaccttca gatgaattcg ttacgcgcag aggataccgc tgtatactac    2160
tgtgctggcg gatcatatta tgtcccagac tattgggggc agggtactct ggtaacggtt    2220
agctct                                                               2226
```

<210> SEQ ID NO 2
<211> LENGTH: 2934
<212> TYPE: DNA
<213> ORGANISM: Artificial
<220> FEATURE:
<223> OTHER INFORMATION: DNA sequence Hexa-AH5Fc

<400> SEQUENCE: 2

| | | | | | |
|---|---|---|---|---|---|
| cagctccagc | tgcaggaaag | cggcggaggc | gtcgtgcagc | ctggcagaag | cctgagactg | 60 |
| agctgtgccg | ccagcggctt | caccttcagc | agctacggca | tgcactgggt | ccgacaggcc | 120 |
| cctggcaaag | aacgggaagg | cgtggccgtg | atcagctacg | acggcagcaa | caagtactac | 180 |
| gccgacagcg | tgaagggccg | gttcaccatc | agccgggaca | acagcaagaa | caccctgtac | 240 |
| ctgcagatga | acagcctgcg | ggccgaggac | accgccgtgt | actattgtgc | cggcggaagc | 300 |
| tactacgtgc | ccgactattg | gggccagggc | accctcgtga | ccgtgtctag | cggcagcacc | 360 |
| agcggctcca | tggctcagct | ccagctccag | gaatctggcg | gcgagtcgt | ccagcccgga | 420 |
| agatctctgc | ggctgtcttg | tgccgcctct | ggctttacct | tctcctccta | tggaatgcat | 480 |
| tgggtccgcc | aggctcccgg | aaaggaaagg | gaaggggtcg | cagtgatctc | ctacgatggc | 540 |
| tccaacaagt | attatgccga | ttctgtgaag | gggcgcttta | ccatctcccg | cgacaactcc | 600 |
| aagaacacac | tctatctcca | gatgaattcc | ctgagagccg | aggatacagc | cgtctattac | 660 |
| tgcgctggcg | gctcctacta | ctgtgcctgat | tactggggac | agggaaccct | ggtcacagtg | 720 |
| tcctccggct | ccaccagcgg | cagtatggca | cagctgcagc | tccaggaatc | tggaggcggg | 780 |
| gtcgtgcagc | caggacgctc | cctgagactg | tcctgtgctg | cctccggatt | cacctttagc | 840 |
| tcttatggga | tgcactgggt | caggcaggca | ccagggaaag | aacgcgaggg | ggtggcagtg | 900 |
| atttcttatg | atgggagcaa | caatatattac | gctgactccg | tcaagggccg | cttcacaatc | 960 |
| tccagagata | attccaagaa | tactctgtac | ctccagatga | attctctgcg | cgctgaggac | 1020 |
| actgctgtct | actactgcgc | aggggggcagc | tattacgtcc | ccgattactg | ggggcagggg | 1080 |
| acactcgtca | ccgtcagcag | cggctctacc | tccggctcta | tggctcagct | gcagctccag | 1140 |
| gaatccgggg | gaggtgtcgt | gcagcctggg | agatccctgc | gcctgagttg | cgccgcttcc | 1200 |
| ggcttcactt | tttcctctta | cggcatgcat | tgggtcaggc | aggctccagg | caaggaacga | 1260 |
| gagggcgtcg | ccgtgatttc | ctatgacgga | tctaacaagt | actatgcaga | ctccgtgaaa | 1320 |
| gggcgattca | ccattagcag | agacaactct | aaaaacactc | tgtatctgca | gatgaattca | 1380 |
| ctccggggcc | aagataccgc | agtgtattac | tgtgcaggcg | gtcttatta | cgtgccagac | 1440 |
| tactggggac | aggggacact | ggtcactgtc | tcaagcggct | ccacctctgg | aagtatggcc | 1500 |
| cagctccagc | tccaggaaag | tggggcgga | gtcgtccagc | caggcagaag | cctcaggctg | 1560 |
| tcttgcgctg | ccagcggatt | cacattttcc | agttacggaa | tgcactgggt | cagacaggct | 1620 |
| cctgaaaggg | aacgcgaagg | tgtcgctgtc | atcagctatg | acgggtccaa | caagtactat | 1680 |
| gctgatagtg | tgaaaggccg | gtttacaatc | tctcgcgata | atagcaagaa | taccctctat | 1740 |
| ctgcagatga | atagtctgag | agctgaggat | accgctgtgt | actactgtgc | tgggggctca | 1800 |
| tattatgtcc | ctgactattg | ggggcaggga | actctcgtca | ctgtgtccag | cggaagcaca | 1860 |
| tccggatcaa | tggcacagct | ccagctgcag | gaaagcggag | gggggtcgt | ccagcctggc | 1920 |
| cgatcactga | gactgtcatg | cgccgccagt | gggtttacat | tcagctccta | cgggatgcat | 1980 |
| tgggtccgcc | aggcacctgg | gaaagagcga | gaaggcgtcg | cagtcattag | ctacgatgga | 2040 |

| | |
|---|---:|
| agtaacaagt attacgcaga tagcgtcaag gggagattca ccatctctag ggacaattcc | 2100 |
| aaaaacaccc tctacctgca gatgaattcc ctgcgggcag aagacaccgc tgtctattat | 2160 |
| tgcgccggag gatcttacta cgtcccagat tattggggac agggcactct ggtcacagtc | 2220 |
| agcagcggat ccacaagcgg cagcggagcc gccgacaaga cccacacctg tccccccttgc | 2280 |
| cctgcccctg agctgctggg aggccctagc gtgttcctgt tccccccaaa gcccaaggac | 2340 |
| accctgatga tcagccggac ccccgaagtg acctgcgtgg tggtggacgt gtcccacgag | 2400 |
| gaccctgaag tgaagttcaa ttggtacgtg gacggcgtgg aagtgcacaa cgccaagacc | 2460 |
| aagcccagag aggaacagta caacagcacc taccgggtgg tgtccgtgct gaccgtgctg | 2520 |
| caccaggact ggctgaacgg caaagagtac aagtgcaagg tctccaacaa ggccctgcct | 2580 |
| gcccccatcg agaaaaccat cagcaaggcc aagggccagc ccgcgagcc tcaggtgtac | 2640 |
| acactgcctc ccagccggga cgagctgacc aagaaccagg tgtccctgac ctgcctggtc | 2700 |
| aagggcttct accccagcga tatcgccgtg gaatgggaga gcaacggcca gcccgagaac | 2760 |
| aactacaaga ccacccccc tgtgctggac agcgacggc cattcttcct gtacagcaag | 2820 |
| ctgaccgtgg acaagagccg gtggcagcag ggcaacgtgt tcagctgctc cgtgatgcac | 2880 |
| gaggccctgc acaaccacta cacccagaag tccctgtccc tgagccccgg caag | 2934 |

<210> SEQ ID NO 3
<211> LENGTH: 4047
<212> TYPE: DNA
<213> ORGANISM: Artificial
<220> FEATURE:
<223> OTHER INFORMATION: DNA sequence Hexa-AH5HSA

<400> SEQUENCE: 3

| | |
|---|---:|
| cagctccagc tgcaggaaag cggcggaggc gtcgtgcagc ctggcagaag cctgagactg | 60 |
| agctgtgccg ccagcggctt caccttcagc agctacggca tgcactgggt ccgacaggcc | 120 |
| cctggcaaag aacggaagg cgtggccgtg atcagctacg acggcagcaa caagtactac | 180 |
| gccgacagcg tgaagggccg gttcaccatc agccgggaca acagcaagaa caccctgtac | 240 |
| ctgcagatga acagcctgcg ggccgaggac accgccgtgt actattgtgc cggcggaagc | 300 |
| tactacgtgc ccgactattg gggccagggc accctcgtga ccgtgtctag cggcagcacc | 360 |
| agcggctcca tggctcagct ccagctccag gaatctggcg gcggagtcgt ccagcccgga | 420 |
| agatctctgc ggctgtcttg tgccgcctct ggctttacct tctcctccta tggaatgcat | 480 |
| tgggtccgcc aggctcccgg aaaggaaagg gaaggggtcg cagtgatctc ctacgatggc | 540 |
| tccaacaagt attatgccga ttctgtgaag gggcgcttta ccatctcccg cgacaactcc | 600 |
| aagaacacac tctatctcca gatgaattcc ctgagagccg aggatacagc cgtctattac | 660 |
| tgcgctggcg gctcctacta ctgtgcctgat tactggggac agggaaccct ggtcacagtg | 720 |
| tcctccggct ccaccagcgg cagtatggca cagctgcagc tccaggaatc tggaggcggg | 780 |
| gtcgtgcagc caggacgctc cctgagactg tcctgtgctg cctccggatt cacctttagc | 840 |
| tcttatggga tgcactgggt caggcaggca ccagggaaag aacgcgaggg ggtggcagtg | 900 |
| atttcttatg atgggagcaa caaatattac gctgactccg tcaagggccg cttcacaatc | 960 |
| tccagagata attccaagaa tactctgtac ctccagatga attctctgcg cgctgaggac | 1020 |
| actgctgtct actactgcgc agggggcagc tattacgtcc ccgattactg ggggcagggg | 1080 |
| acactcgtca ccgtcagcag cggctctacc tccggctcta tggctcagct gcagctccag | 1140 |
| gaatccgggg gaggtgtcgt gcagcctggg agatccctgc gcctgagttg cgccgcttcc | 1200 |

```
ggcttcactt tttcctctta cggcatgcat tgggtcaggc aggctccagg caaggaacga   1260
gagggcgtcg ccgtgatttc ctatgacgga tctaacaagt actatgcaga ctccgtgaaa   1320
gggcgattca ccattagcag agacaactct aaaaacactc tgtatctgca gatgaattca   1380
ctccgggccg aagataccgc agtgtattac tgtgcaggcg ggtcttatta cgtgccagac   1440
tactggggac aggggacact ggtcactgtc tcaagcggct ccacctctgg aagtatggcc   1500
cagctccagc tccaggaaag tgggggcgga gtcgtccagc caggcagaag cctcaggctg   1560
tcttgcgctg ccagcggatt cacattttcc agttacggaa tgcactgggt cagacaggct   1620
cctggaaagg aacgcgaagg tgtcgctgtc atcagctatg acgggtccaa caagtactat   1680
gctgatagtg tgaaaggccg gtttacaatc tctcgcgata atagcaagaa taccctctat   1740
ctgcagatga atagtctgag agctgaggat accgctgtgt actactgtgc tgggggctca   1800
tattatgtcc ctgactattg ggggcaggga actctcgtca ctgtgtccag cggaagcaca   1860
tccggatcaa tggcacagct ccagctgcag gaaagcggag gggggtcgt ccagcctggc    1920 cgatcactga gactgtcatg cgccgccagt gggtttacat tcagctccta cgggatgcat   1980
tgggtccgcc aggcacctgg aaagagcga gaaggcgtcg cagtcattag ctacgatgga    2040
agtaacaagt attacgcaga tagcgtcaag gggagattca ccatctctag gacaattcc    2100 aaaaacaccc tctacctgca gatgaattcc ctgcgggcag aagacaccgc tgtctattat   2160
tgcgccggag gatcttacta cgtcccagat tattgggac agggcactct ggtcacagtc    2220
agcagcggat ccacaagcgg cagcggagcc gctggaggcg atctggcgg cagagcttct    2280 ggcggaggca gcgacgccca agagcgaa gtggcccaca gattcaagga cctgggcgag     2340
gaaaacttca aggccctggt gctgattgcc ttcgcccagt acctgcagca gtgccccttc   2400
gaggaccacg tgaagctggt caacgaagtg accgagttcg ccaagacctg cgtggccgac   2460
gagagcgccg agaactgcga caagagcctg cacaccctgt tcggcgacaa gctgtgcacc   2520
gtggccaccc tgcgggaaac ctacggcgag atggccgact gctgcgccaa gcaggaaccc   2580
gagcggaacg agtgcttcct gcagcacaag gacgacaacc ccaacctgcc cagactcgtg   2640
cggcccgagg tggacgtgat gtgcaccgcc ttccacgaca cgaggaaaac cttcctgaag   2700
aagtacctgt acgagatcgc cagacggcac ccctacttct acgcccccga gctgctgttc   2760
ttcgccaagc ggtacaaggc cgccttcacc gagtgctgcc aggccgccga taaggccgcc   2820
tgcctgctgc ccaagctgga cgagctgcgg gatgagggca aggccagctc cgccaagcag   2880
agactgaagt gcgccagcct gcagaagttc ggcgagcggg cctttaaggc ctgggccgtg   2940
gccagactga ccagagatt ccccaaggcc gagtttgccg aggtgtccaa gctggtcacc    3000
gacctgacca aggtgcacac cgagtgttgt cacggcgacc tgctggaatg cgccgacgac   3060
agagccgatc tggccaagta catctgcgag aaccaggaca gcatcagcag caagctgaaa   3120
gagtgctgcg agaagcccct gctggaaaag agccactgta tcgccgaggt ggaaaacgac   3180
gagatgcccg ccgacctgcc tagcctggcc gccgattcg tggaaagcaa ggacgtgtgc    3240
aagaattacg ccgaggccaa ggatgtgttc ctgggcatgt tcctgtatga gtacgccagg   3300 cgccacccg actacagcgt ggtcctgctg ctgcggctgg ccaagaccta cgagacaacc   3360
ctggaaaagt gctgcgccgc tgccgacccc cacgagtgtt acgccaaggt gttcgacgag   3420
ttcaagcctc tggtggaaga cccccagaac ctgatcaagc agaactgcga gctgttcgag   3480
cagctgggcg agtacaagtt ccagaacgcc ctgctcgtgc ggtacaccaa gaaggtgccc   3540
```

```
caggtcagca ccccccaccct ggtggaagtg tcccggaacc tgggcaaagt gggcagcaag   3600
tgctgcaagc accctgaggc caagcggatg ccctgcgccg aggactacct gagcgtggtg   3660
ctgaaccagc tgtgcgtgct gcacgagaaa accccgtgt ccgacagagt gaccaagtgc    3720
tgtaccgaga gcctggtcaa cagacggccc tgcttcagcg ccctggaagt ggacgagaca   3780
tacgtgccca agagttcaa cgccgagaca ttcaccttcc acgccgacat ctgcaccctg    3840
agcgagaaag agcggcagat caagaaacag accgcactgg tggaactggt caagcacaag   3900
cccaaggcca ccaaagaaca gctgaaggcc gtgatggacg acttcgccgc cttcgtggaa   3960
aagtgttgca aggccgacga caaagagaca tgcttcgccg aagagggcaa gaaactggtg   4020
gccgccagtc aggccgctct gggactg                                       4047
```

<210> SEQ ID NO 4
<211> LENGTH: 742
<212> TYPE: PRT
<213> ORGANISM: Artificial
<220> FEATURE:
<223> OTHER INFORMATION: Amino acid sequence hexa-AH5

<400> SEQUENCE: 4

```
Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Arg Glu Gly Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ser Tyr Tyr Val Pro Asp Tyr Trp Gly Gln Gly Thr Leu
            100                 105                 110

Val Thr Val Ser Ser Gly Ser Thr Ser Gly Ser Met Ala Gln Leu Gln
        115                 120                 125

Leu Gln Glu Ser Gly Gly Gly Val Val Gln Pro Gly Arg Ser Leu Arg
    130                 135                 140

Leu Ser Cys Ala Ala Ser Gly Phe Thr Phe Ser Ser Tyr Gly Met His
145                 150                 155                 160

Trp Val Arg Gln Ala Pro Gly Lys Glu Arg Glu Gly Val Ala Val Ile
                165                 170                 175

Ser Tyr Asp Gly Ser Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Gly Gly
    210                 215                 220

Ser Tyr Tyr Val Pro Asp Tyr Trp Gly Gln Gly Thr Leu Val Thr Val
225                 230                 235                 240

Ser Ser Gly Ser Thr Ser Gly Ser Met Ala Gln Leu Gln Leu Gln Glu
                245                 250                 255

Ser Gly Gly Gly Val Val Gln Pro Gly Arg Ser Leu Arg Leu Ser Cys
            260                 265                 270
```

-continued

Ala Ala Ser Gly Phe Thr Phe Ser Ser Tyr Gly Met His Trp Val Arg
            275                 280                 285

Gln Ala Pro Gly Lys Glu Arg Glu Gly Val Ala Val Ile Ser Tyr Asp
        290                 295                 300

Gly Ser Asn Lys Tyr Tyr Ala Asp Ser Val Lys Gly Arg Phe Thr Ile
305                 310                 315                 320

Ser Arg Asp Asn Ser Lys Asn Thr Leu Tyr Leu Gln Met Asn Ser Leu
                325                 330                 335

Arg Ala Glu Asp Thr Ala Val Tyr Tyr Cys Ala Gly Gly Ser Tyr Tyr
            340                 345                 350

Val Pro Asp Tyr Trp Gly Gln Gly Thr Leu Val Thr Val Ser Ser Gly
        355                 360                 365

Ser Thr Ser Gly Ser Met Ala Gln Leu Gln Leu Gln Glu Ser Gly Gly
    370                 375                 380

Gly Val Val Gln Pro Gly Arg Ser Leu Arg Leu Ser Cys Ala Ala Ser
385                 390                 395                 400

Gly Phe Thr Phe Ser Ser Tyr Gly Met His Trp Val Arg Gln Ala Pro
                405                 410                 415

Gly Lys Glu Arg Glu Gly Val Ala Val Ile Ser Tyr Asp Gly Ser Asn
            420                 425                 430

Lys Tyr Tyr Ala Asp Ser Val Lys Gly Arg Phe Thr Ile Ser Arg Asp
        435                 440                 445

Asn Ser Lys Asn Thr Leu Tyr Leu Gln Met Asn Ser Leu Arg Ala Glu
    450                 455                 460

Asp Thr Ala Val Tyr Tyr Cys Ala Gly Gly Ser Tyr Tyr Val Pro Asp
465                 470                 475                 480

Tyr Trp Gly Gln Gly Thr Leu Val Thr Val Ser Ser Gly Ser Thr Ser
                485                 490                 495

Gly Ser Met Ala Gln Leu Gln Leu Gln Glu Ser Gly Gly Gly Val Val
            500                 505                 510

Gln Pro Gly Arg Ser Leu Arg Leu Ser Cys Ala Ala Ser Gly Phe Thr
        515                 520                 525

Phe Ser Ser Tyr Gly Met His Trp Val Arg Gln Ala Pro Gly Lys Glu
    530                 535                 540

Arg Glu Gly Val Ala Val Ile Ser Tyr Asp Gly Ser Asn Lys Tyr Tyr
545                 550                 555                 560

Ala Asp Ser Val Lys Gly Arg Phe Thr Ile Ser Arg Asp Asn Ser Lys
                565                 570                 575

Asn Thr Leu Tyr Leu Gln Met Asn Ser Leu Arg Ala Glu Asp Thr Ala
            580                 585                 590

Val Tyr Tyr Cys Ala Gly Gly Ser Tyr Tyr Val Pro Asp Tyr Trp Gly
        595                 600                 605

Gln Gly Thr Leu Val Thr Val Ser Ser Gly Ser Thr Ser Gly Ser Met
    610                 615                 620

Ala Gln Leu Gln Leu Gln Glu Ser Gly Gly Gly Val Val Gln Pro Gly
625                 630                 635                 640

Arg Ser Leu Arg Leu Ser Cys Ala Ala Ser Gly Phe Thr Phe Ser Ser
                645                 650                 655

Tyr Gly Met His Trp Val Arg Gln Ala Pro Gly Lys Glu Arg Glu Gly
            660                 665                 670

Val Ala Val Ile Ser Tyr Asp Gly Ser Asn Lys Tyr Tyr Ala Asp Ser
        675                 680                 685

Val Lys Gly Arg Phe Thr Ile Ser Arg Asp Asn Ser Lys Asn Thr Leu

```
              690                 695                 700
Tyr Leu Gln Met Asn Ser Leu Arg Ala Glu Asp Thr Ala Val Tyr Tyr
705                 710                 715                 720

Cys Ala Gly Gly Ser Tyr Tyr Val Pro Asp Tyr Trp Gly Gln Gly Thr
                725                 730                 735

Leu Val Thr Val Ser Ser
            740

<210> SEQ ID NO 5
<211> LENGTH: 978
<212> TYPE: PRT
<213> ORGANISM: Artificial
<220> FEATURE:
<223> OTHER INFORMATION: Amino acid sequence Hexa-AH5Fc

<400> SEQUENCE: 5

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Arg Glu Gly Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Gly Gly Ser Tyr Tyr Val Pro Asp Tyr Trp Gly Gln Gly Thr Leu
        100                 105                 110

Val Thr Val Ser Ser Gly Ser Thr Ser Gly Ser Met Ala Gln Leu Gln
    115                 120                 125

Leu Gln Glu Ser Gly Gly Gly Val Val Gln Pro Gly Arg Ser Leu Arg
130                 135                 140

Leu Ser Cys Ala Ala Ser Gly Phe Thr Phe Ser Ser Tyr Gly Met His
145                 150                 155                 160

Trp Val Arg Gln Ala Pro Gly Lys Glu Arg Glu Gly Val Ala Val Ile
            165                 170                 175

Ser Tyr Asp Gly Ser Asn Lys Tyr Tyr Ala Asp Ser Val Lys Gly Arg
        180                 185                 190

Phe Thr Ile Ser Arg Asp Asn Ser Lys Asn Thr Leu Tyr Leu Gln Met
    195                 200                 205

Asn Ser Leu Arg Ala Glu Asp Thr Ala Val Tyr Tyr Cys Ala Gly Gly
210                 215                 220

Ser Tyr Tyr Val Pro Asp Tyr Trp Gly Gln Gly Thr Leu Val Thr Val
225                 230                 235                 240

Ser Ser Gly Ser Thr Ser Gly Ser Met Ala Gln Leu Gln Leu Gln Glu
            245                 250                 255

Ser Gly Gly Gly Val Val Gln Pro Gly Arg Ser Leu Arg Leu Ser Cys
        260                 265                 270

Ala Ala Ser Gly Phe Thr Phe Ser Ser Tyr Gly Met His Trp Val Arg
    275                 280                 285

Gln Ala Pro Gly Lys Glu Arg Glu Gly Val Ala Val Ile Ser Tyr Asp
290                 295                 300

Gly Ser Asn Lys Tyr Tyr Ala Asp Ser Val Lys Gly Arg Phe Thr Ile
```

```
          305                 310                 315                 320
Ser Arg Asp Asn Ser Lys Asn Thr Leu Tyr Leu Gln Met Asn Ser Leu
                325                 330                 335
Arg Ala Glu Asp Thr Ala Val Tyr Tyr Cys Ala Gly Gly Ser Tyr Tyr
                340                 345                 350
Val Pro Asp Tyr Trp Gly Gln Gly Thr Leu Val Thr Val Ser Ser Gly
                355                 360                 365
Ser Thr Ser Gly Ser Met Ala Gln Leu Gln Leu Gln Glu Ser Gly Gly
                370                 375                 380
Gly Val Val Gln Pro Gly Arg Ser Leu Arg Leu Ser Cys Ala Ala Ser
385                 390                 395                 400
Gly Phe Thr Phe Ser Ser Tyr Gly Met His Trp Val Arg Gln Ala Pro
                405                 410                 415
Gly Lys Glu Arg Glu Gly Val Ala Val Ile Ser Tyr Asp Gly Ser Asn
                420                 425                 430
Lys Tyr Tyr Ala Asp Ser Val Lys Gly Arg Phe Thr Ile Ser Arg Asp
                435                 440                 445
Asn Ser Lys Asn Thr Leu Tyr Leu Gln Met Asn Ser Leu Arg Ala Glu
                450                 455                 460
Asp Thr Ala Val Tyr Tyr Cys Ala Gly Gly Ser Tyr Tyr Val Pro Asp
465                 470                 475                 480
Tyr Trp Gly Gln Gly Thr Leu Val Thr Val Ser Ser Gly Ser Thr Ser
                485                 490                 495
Gly Ser Met Ala Gln Leu Gln Leu Gln Glu Ser Gly Gly Gly Val Val
                500                 505                 510
Gln Pro Gly Arg Ser Leu Arg Leu Ser Cys Ala Ala Ser Gly Phe Thr
                515                 520                 525
Phe Ser Ser Tyr Gly Met His Trp Val Arg Gln Ala Pro Gly Lys Glu
                530                 535                 540
Arg Glu Gly Val Ala Val Ile Ser Tyr Asp Gly Ser Asn Lys Tyr Tyr
545                 550                 555                 560
Ala Asp Ser Val Lys Gly Arg Phe Thr Ile Ser Arg Asp Asn Ser Lys
                565                 570                 575
Asn Thr Leu Tyr Leu Gln Met Asn Ser Leu Arg Ala Glu Asp Thr Ala
                580                 585                 590
Val Tyr Tyr Cys Ala Gly Gly Ser Tyr Tyr Val Pro Asp Tyr Trp Gly
                595                 600                 605
Gln Gly Thr Leu Val Thr Val Ser Ser Gly Ser Thr Ser Gly Ser Met
                610                 615                 620
Ala Gln Leu Gln Leu Gln Glu Ser Gly Gly Gly Val Val Gln Pro Gly
625                 630                 635                 640
Arg Ser Leu Arg Leu Ser Cys Ala Ala Ser Gly Phe Thr Phe Ser Ser
                645                 650                 655
Tyr Gly Met His Trp Val Arg Gln Ala Pro Gly Lys Glu Arg Glu Gly
                660                 665                 670
Val Ala Val Ile Ser Tyr Asp Gly Ser Asn Lys Tyr Tyr Ala Asp Ser
                675                 680                 685
Val Lys Gly Arg Phe Thr Ile Ser Arg Asp Asn Ser Lys Asn Thr Leu
                690                 695                 700
Tyr Leu Gln Met Asn Ser Leu Arg Ala Glu Asp Thr Ala Val Tyr Tyr
705                 710                 715                 720
Cys Ala Gly Gly Ser Tyr Tyr Val Pro Asp Tyr Trp Gly Gln Gly Thr
                725                 730                 735
```

```
Leu Val Thr Val Ser Ser Gly Ser Thr Ser Gly Ser Gly Ala Ala Asp
                740                 745                 750

Lys Thr His Thr Cys Pro Pro Cys Pro Ala Pro Glu Leu Leu Gly Gly
            755                 760                 765

Pro Ser Val Phe Leu Phe Pro Pro Lys Pro Lys Asp Thr Leu Met Ile
        770                 775                 780

Ser Arg Thr Pro Glu Val Thr Cys Val Val Val Asp Val Ser His Glu
785                 790                 795                 800

Asp Pro Glu Val Lys Phe Asn Trp Tyr Val Asp Gly Val Glu Val His
                805                 810                 815

Asn Ala Lys Thr Lys Pro Arg Glu Glu Gln Tyr Asn Ser Thr Tyr Arg
            820                 825                 830

Val Val Ser Val Leu Thr Val Leu His Gln Asp Trp Leu Asn Gly Lys
        835                 840                 845

Glu Tyr Lys Cys Lys Val Ser Asn Lys Ala Leu Pro Ala Pro Ile Glu
850                 855                 860

Lys Thr Ile Ser Lys Ala Lys Gly Gln Pro Arg Glu Pro Gln Val Tyr
                865                 870                 875                 880

Thr Leu Pro Pro Ser Arg Asp Glu Leu Thr Lys Asn Gln Val Ser Leu
            885                 890                 895

Thr Cys Leu Val Lys Gly Phe Tyr Pro Ser Asp Ile Ala Val Glu Trp
        900                 905                 910

Glu Ser Asn Gly Gln Pro Glu Asn Asn Tyr Lys Thr Thr Pro Pro Val
        915                 920                 925

Leu Asp Ser Asp Gly Ser Phe Phe Leu Tyr Ser Lys Leu Thr Val Asp
        930                 935                 940

Lys Ser Arg Trp Gln Gln Gly Asn Val Phe Ser Cys Ser Val Met His
945                 950                 955                 960

Glu Ala Leu His Asn His Tyr Thr Gln Lys Ser Leu Ser Leu Ser Pro
                965                 970                 975

Gly Lys

<210> SEQ ID NO 6
<211> LENGTH: 1349
<212> TYPE: PRT
<213> ORGANISM: Artificial
<220> FEATURE:
<223> OTHER INFORMATION: Amino acid sequence Hexa-AH5HSA

<400> SEQUENCE: 6

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Glu Arg Glu Gly Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ser Tyr Tyr Val Pro Asp Tyr Trp Gly Gln Gly Thr Leu
            100                 105                 110
```

-continued

Val Thr Val Ser Ser Gly Ser Thr Gly Ser Met Ala Gln Leu Gln
            115                 120             125

Leu Gln Glu Ser Gly Gly Val Val Gln Pro Gly Arg Ser Leu Arg
        130                 135             140

Leu Ser Cys Ala Ala Ser Gly Phe Thr Phe Ser Ser Tyr Gly Met His
145                 150                 155                 160

Trp Val Arg Gln Ala Pro Gly Lys Glu Arg Glu Gly Val Ala Val Ile
                165                 170                 175

Ser Tyr Asp Gly Ser Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Gly Gly
210                 215                 220

Ser Tyr Tyr Val Pro Asp Tyr Trp Gly Gln Gly Thr Leu Val Thr Val
225                 230                 235                 240

Ser Ser Gly Ser Thr Gly Ser Met Ala Gln Leu Gln Leu Gln Glu
                245                 250                 255

Ser Gly Gly Gly Val Val Gln Pro Gly Arg Ser Leu Arg Leu Ser Cys
            260                 265                 270

Ala Ala Ser Gly Phe Thr Phe Ser Ser Tyr Gly Met His Trp Val Arg
        275                 280                 285

Gln Ala Pro Gly Lys Glu Arg Glu Gly Val Ala Val Ile Ser Tyr Asp
        290                 295                 300

Gly Ser Asn Lys Tyr Tyr Ala Asp Ser Val Lys Gly Arg Phe Thr Ile
305                 310                 315                 320

Ser Arg Asp Asn Ser Lys Asn Thr Leu Tyr Leu Gln Met Asn Ser Leu
                325                 330                 335

Arg Ala Glu Asp Thr Ala Val Tyr Tyr Cys Ala Gly Gly Ser Tyr Tyr
            340                 345                 350

Val Pro Asp Tyr Trp Gly Gln Gly Thr Leu Val Thr Val Ser Ser Gly
        355                 360                 365

Ser Thr Gly Ser Met Ala Gln Leu Gln Leu Gln Glu Ser Gly Gly
370                 375                 380

Gly Val Val Gln Pro Gly Arg Ser Leu Arg Leu Ser Cys Ala Ala Ser
385                 390                 395                 400

Gly Phe Thr Phe Ser Ser Tyr Gly Met His Trp Val Arg Gln Ala Pro
                405                 410                 415

Gly Lys Glu Arg Glu Gly Val Ala Val Ile Ser Tyr Asp Gly Ser Asn
            420                 425                 430

Lys Tyr Tyr Ala Asp Ser Val Lys Gly Arg Phe Thr Ile Ser Arg Asp
        435                 440                 445

Asn Ser Lys Asn Thr Leu Tyr Leu Gln Met Asn Ser Leu Arg Ala Glu
        450                 455                 460

Asp Thr Ala Val Tyr Tyr Cys Ala Gly Gly Ser Tyr Tyr Val Pro Asp
465                 470                 475                 480

Tyr Trp Gly Gln Gly Thr Leu Val Thr Val Ser Ser Gly Ser Thr Ser
                485                 490                 495

Gly Ser Met Ala Gln Leu Gln Leu Gln Glu Ser Gly Gly Val Val
            500                 505                 510

Gln Pro Gly Arg Ser Leu Arg Leu Ser Cys Ala Ala Ser Gly Phe Thr
        515                 520                 525

Phe Ser Ser Tyr Gly Met His Trp Val Arg Gln Ala Pro Gly Lys Glu

```
                530                 535                 540
Arg Glu Gly Val Ala Val Ile Ser Tyr Asp Gly Ser Asn Lys Tyr Tyr
545                 550                 555                 560

Ala Asp Ser Val Lys Gly Arg Phe Thr Ile Ser Arg Asp Asn Ser Lys
                565                 570                 575

Asn Thr Leu Tyr Leu Gln Met Asn Ser Leu Arg Ala Glu Asp Thr Ala
                580                 585                 590

Val Tyr Tyr Cys Ala Gly Gly Ser Tyr Tyr Val Pro Asp Tyr Trp Gly
                595                 600                 605

Gln Gly Thr Leu Val Thr Val Ser Ser Gly Ser Thr Ser Gly Ser Met
610                 615                 620

Ala Gln Leu Gln Leu Gln Glu Ser Gly Gly Gly Val Val Gln Pro Gly
625                 630                 635                 640

Arg Ser Leu Arg Leu Ser Cys Ala Ala Ser Gly Phe Thr Phe Ser Ser
                645                 650                 655

Tyr Gly Met His Trp Val Arg Gln Ala Pro Gly Lys Glu Arg Glu Gly
                660                 665                 670

Val Ala Val Ile Ser Tyr Asp Gly Ser Asn Lys Tyr Tyr Ala Asp Ser
                675                 680                 685

Val Lys Gly Arg Phe Thr Ile Ser Arg Asp Asn Ser Lys Asn Thr Leu
                690                 695                 700

Tyr Leu Gln Met Asn Ser Leu Arg Ala Glu Asp Thr Ala Val Tyr Tyr
705                 710                 715                 720

Cys Ala Gly Gly Ser Tyr Tyr Val Pro Asp Tyr Trp Gly Gln Gly Thr
                725                 730                 735

Leu Val Thr Val Ser Ser Gly Ser Thr Ser Gly Ser Gly Ala Ala Gly
                740                 745                 750

Gly Gly Ser Gly Gly Arg Ala Ser Gly Gly Gly Ser Asp Ala His Lys
                755                 760                 765

Ser Glu Val Ala His Arg Phe Lys Asp Leu Gly Glu Glu Asn Phe Lys
770                 775                 780

Ala Leu Val Leu Ile Ala Phe Ala Gln Tyr Leu Gln Gln Cys Pro Phe
785                 790                 795                 800

Glu Asp His Val Lys Leu Val Asn Glu Val Thr Glu Phe Ala Lys Thr
                805                 810                 815

Cys Val Ala Asp Glu Ser Ala Glu Asn Cys Asp Lys Ser Leu His Thr
                820                 825                 830

Leu Phe Gly Asp Lys Leu Cys Thr Val Ala Thr Leu Arg Glu Thr Tyr
                835                 840                 845

Gly Glu Met Ala Asp Cys Cys Ala Lys Gln Glu Pro Glu Arg Asn Glu
850                 855                 860

Cys Phe Leu Gln His Lys Asp Asp Asn Pro Asn Leu Pro Arg Leu Val
865                 870                 875                 880

Arg Pro Glu Val Asp Val Met Cys Thr Ala Phe His Asp Asn Glu Glu
                885                 890                 895

Thr Phe Leu Lys Lys Tyr Leu Tyr Glu Ile Ala Arg Arg His Pro Tyr
                900                 905                 910

Phe Tyr Ala Pro Glu Leu Leu Phe Phe Ala Lys Arg Tyr Lys Ala Ala
                915                 920                 925

Phe Thr Glu Cys Cys Gln Ala Ala Asp Lys Ala Ala Cys Leu Leu Pro
930                 935                 940

Lys Leu Asp Glu Leu Arg Asp Glu Gly Lys Ala Ser Ser Ala Lys Gln
945                 950                 955                 960
```

```
Arg Leu Lys Cys Ala Ser Leu Gln Lys Phe Gly Glu Arg Ala Phe Lys
            965                 970                 975

Ala Trp Ala Val Ala Arg Leu Ser Gln Arg Phe Pro Lys Ala Glu Phe
        980                 985                 990

Ala Glu Val Ser Lys Leu Val Thr Asp Leu Thr Lys Val His Thr Glu
    995                 1000                1005

Cys Cys His Gly Asp Leu Leu Glu Cys Ala Asp Asp Arg Ala Asp
1010                1015                1020

Leu Ala Lys Tyr Ile Cys Glu Asn Gln Asp Ser Ile Ser Ser Lys
1025                1030                1035

Leu Lys Glu Cys Cys Glu Lys Pro Leu Leu Glu Lys Ser His Cys
1040                1045                1050

Ile Ala Glu Val Glu Asn Asp Glu Met Pro Ala Asp Leu Pro Ser
1055                1060                1065

Leu Ala Ala Asp Phe Val Glu Ser Lys Asp Val Cys Lys Asn Tyr
1070                1075                1080

Ala Glu Ala Lys Asp Val Phe Leu Gly Met Phe Leu Tyr Glu Tyr
1085                1090                1095

Ala Arg Arg His Pro Asp Tyr Ser Val Val Leu Leu Leu Arg Leu
1100                1105                1110

Ala Lys Thr Tyr Glu Thr Thr Leu Glu Lys Cys Cys Ala Ala Ala
1115                1120                1125

Asp Pro His Glu Cys Tyr Ala Lys Val Phe Asp Glu Phe Lys Pro
1130                1135                1140

Leu Val Glu Glu Pro Gln Asn Leu Ile Lys Gln Asn Cys Glu Leu
1145                1150                1155

Phe Glu Gln Leu Gly Glu Tyr Lys Phe Gln Asn Ala Leu Leu Val
1160                1165                1170

Arg Tyr Thr Lys Lys Val Pro Gln Val Ser Thr Pro Thr Leu Val
1175                1180                1185

Glu Val Ser Arg Asn Leu Gly Lys Val Gly Ser Lys Cys Cys Lys
1190                1195                1200

His Pro Glu Ala Lys Arg Met Pro Cys Ala Glu Asp Tyr Leu Ser
1205                1210                1215

Val Val Leu Asn Gln Leu Cys Val Leu His Glu Lys Thr Pro Val
1220                1225                1230

Ser Asp Arg Val Thr Lys Cys Cys Thr Glu Ser Leu Val Asn Arg
1235                1240                1245

Arg Pro Cys Phe Ser Ala Leu Glu Val Asp Glu Thr Tyr Val Pro
1250                1255                1260

Lys Glu Phe Asn Ala Glu Thr Phe Thr Phe His Ala Asp Ile Cys
1265                1270                1275

Thr Leu Ser Glu Lys Glu Arg Gln Ile Lys Lys Gln Thr Ala Leu
1280                1285                1290

Val Glu Leu Val Lys His Lys Pro Lys Ala Thr Lys Glu Gln Leu
1295                1300                1305

Lys Ala Val Met Asp Asp Phe Ala Ala Phe Val Glu Lys Cys Cys
1310                1315                1320

Lys Ala Asp Asp Lys Glu Thr Cys Phe Ala Glu Glu Gly Lys Lys
1325                1330                1335

Leu Val Ala Ala Ser Gln Ala Ala Leu Gly Leu
1340                1345
```

```
<210> SEQ ID NO 7
<211> LENGTH: 9
<212> TYPE: PRT
<213> ORGANISM: Artificial
<220> FEATURE:
<223> OTHER INFORMATION: Amino acid sequence MHC-1 HLA-A0201 presentable
      peptide in MAGE-A

<400> SEQUENCE: 7

Tyr Leu Glu Tyr Arg Gln Val Pro Gly
1               5

<210> SEQ ID NO 8
<211> LENGTH: 9
<212> TYPE: PRT
<213> ORGANISM: Artificial
<220> FEATURE:
<223> OTHER INFORMATION: Amino acid sequence MHC-1 HLA-CW7 presentable
      peptide in MAGE-A

<400> SEQUENCE: 8

Glu Gly Asp Cys Ala Pro Glu Glu Lys
1               5

<210> SEQ ID NO 9
<211> LENGTH: 9
<212> TYPE: PRT
<213> ORGANISM: Artificial
<220> FEATURE:
<223> OTHER INFORMATION: Amino acid sequence MHC-1 HLA-A0201 presentable
      peptide in MAGE-A1

<400> SEQUENCE: 9

Tyr Leu Glu Tyr Arg Gln Val Pro Asp
1               5

<210> SEQ ID NO 10
<211> LENGTH: 9
<212> TYPE: PRT
<213> ORGANISM: Artificial
<220> FEATURE:
<223> OTHER INFORMATION: Amino acid sequence MHC-1 HLA-A0201 presentable
      peptide in MAGE-A1, with enhanced binding capacity for HLA-A0201

<400> SEQUENCE: 10

Tyr Leu Glu Tyr Arg Gln Val Pro Val
1               5

<210> SEQ ID NO 11
<211> LENGTH: 117
<212> TYPE: PRT
<213> ORGANISM: Artificial
<220> FEATURE:
<223> OTHER INFORMATION: Amino acid sequence Vh-AH5

<400> SEQUENCE: 11

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Arg Glu Gly Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

```
                     65                  70                  75                  80
Leu Gln Met Asn Ser Leu Arg Ala Glu Asp Thr Ala Val Tyr Tyr Cys
                85                  90                  95

Ala Gly Gly Ser Tyr Tyr Val Pro Asp Tyr Trp Gly Gln Gly Thr Leu
                100                 105                 110

Val Thr Val Ser Ser
            115

<210> SEQ ID NO 12
<211> LENGTH: 121
<212> TYPE: PRT
<213> ORGANISM: Artificial
<220> FEATURE:
<223> OTHER INFORMATION: Amino acid sequence Vh-11H

<400> SEQUENCE: 12

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Leu
                35                  40                  45

Ser Tyr Ile Ser Ser Asp Gly Ser Thr Ile Tyr Tyr Ala Asp Ser Val
            50                  55                  60

Lys Gly Arg Phe Thr Val Ser Arg Asp Asn Ala Lys Asn Ser Leu Ser
65                  70                  75                  80

Leu Gln Met Asn Ser Leu Arg Ala Asp Asp Thr Ala Val Tyr Tyr Cys
                85                  90                  95

Ala Val Ser Pro Arg Gly Tyr Tyr Tyr Gly Leu Asp Leu Trp Gly
                100                 105                 110

Gln Gly Thr Thr Val Thr Val Ser Ser
            115                 120

<210> SEQ ID NO 13
<211> LENGTH: 884
<212> TYPE: PRT
<213> ORGANISM: Artificial
<220> FEATURE:
<223> OTHER INFORMATION: Amino acid sequence of Hexa-11HCH1

<400> SEQUENCE: 13

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Leu
                35                  40                  45

Ser Tyr Ile Ser Ser Asp Gly Ser Thr Ile Tyr Tyr Ala Asp Ser Val
            50                  55                  60

Lys Gly Arg Phe Thr Val Ser Arg Asp Asn Ala Lys Asn Ser Leu Ser
65                  70                  75                  80

Leu Gln Met Asn Ser Leu Arg Ala Asp Asp Thr Ala Val Tyr Tyr Cys
                85                  90                  95

Ala Val Ser Pro Arg Gly Tyr Tyr Tyr Gly Leu Asp Leu Trp Gly
                100                 105                 110

Gln Gly Thr Thr Val Thr Val Ser Ser Glu Pro Lys Ser Cys Asp Lys
            115                 120                 125
```

```
Thr His Thr Ala Glu Val Gln Leu Val Gln Ser Gly Gly Leu Val
130                 135                 140
Lys Pro Gly Gly Ser Leu Arg Leu Ser Cys Ala Ala Ser Gly Phe Thr
145                 150                 155                 160
Phe Ser Asp Tyr Tyr Met Ser Trp Ile Arg Gln Ala Pro Gly Lys Gly
                165                 170                 175
Leu Glu Trp Leu Ser Tyr Ile Ser Ser Asp Gly Ser Thr Ile Tyr Tyr
            180                 185                 190
Ala Asp Ser Val Lys Gly Arg Phe Thr Val Ser Arg Asp Asn Ala Lys
        195                 200                 205
Asn Ser Leu Ser Leu Gln Met Asn Ser Leu Arg Ala Asp Asp Thr Ala
210                 215                 220
Val Tyr Tyr Cys Ala Val Ser Pro Arg Gly Tyr Tyr Tyr Gly Leu
225                 230                 235                 240
Asp Leu Trp Gly Gln Gly Thr Thr Val Thr Val Ser Ser Glu Pro Lys
                245                 250                 255
Ser Cys Asp Lys Thr His Thr Ala Glu Val Gln Leu Val Gln Ser Gly
            260                 265                 270
Gly Gly Leu Val Lys Pro Gly Gly Ser Leu Arg Leu Ser Cys Ala Ala
        275                 280                 285
Ser Gly Phe Thr Phe Ser Asp Tyr Tyr Met Ser Trp Ile Arg Gln Ala
290                 295                 300
Pro Gly Lys Gly Leu Glu Trp Leu Ser Tyr Ile Ser Ser Asp Gly Ser
305                 310                 315                 320
Thr Ile Tyr Tyr Ala Asp Ser Val Lys Gly Arg Phe Thr Val Ser Arg
                325                 330                 335
Asp Asn Ala Lys Asn Ser Leu Ser Leu Gln Met Asn Ser Leu Arg Ala
            340                 345                 350
Asp Asp Thr Ala Val Tyr Tyr Cys Ala Val Ser Pro Arg Gly Tyr Tyr
        355                 360                 365
Tyr Tyr Gly Leu Asp Leu Trp Gly Gln Gly Thr Thr Val Thr Val Ser
370                 375                 380
Ser Glu Pro Lys Ser Cys Asp Lys Thr His Thr Ala Glu Val Gln Leu
385                 390                 395                 400
Val Gln Ser Gly Gly Gly Leu Val Lys Pro Gly Gly Ser Leu Arg Leu
                405                 410                 415
Ser Cys Ala Ala Ser Gly Phe Thr Phe Ser Asp Tyr Tyr Met Ser Trp
            420                 425                 430
Ile Arg Gln Ala Pro Gly Lys Gly Leu Glu Trp Leu Ser Tyr Ile Ser
        435                 440                 445
Ser Asp Gly Ser Thr Ile Tyr Tyr Ala Asp Ser Val Lys Gly Arg Phe
450                 455                 460
Thr Val Ser Arg Asp Asn Ala Lys Asn Ser Leu Ser Leu Gln Met Asn
465                 470                 475                 480
Ser Leu Arg Ala Asp Asp Thr Ala Val Tyr Tyr Cys Ala Val Ser Pro
                485                 490                 495
Arg Gly Tyr Tyr Tyr Tyr Gly Leu Asp Leu Trp Gly Gln Gly Thr Thr
            500                 505                 510
Val Thr Val Ser Ser Glu Pro Lys Ser Cys Asp Lys Thr His Thr Ala
        515                 520                 525
Glu Val Gln Leu Val Gln Ser Gly Gly Gly Leu Val Lys Pro Gly Gly
530                 535                 540

Ser Leu Arg Leu Ser Cys Ala Ala Ser Gly Phe Thr Phe Ser Asp Tyr
```

```
                545                 550                 555                 560
Tyr Met Ser Trp Ile Arg Gln Ala Pro Gly Lys Gly Leu Glu Trp Leu
                    565                 570                 575
Ser Tyr Ile Ser Ser Asp Gly Ser Thr Ile Tyr Tyr Ala Asp Ser Val
                580                 585                 590
Lys Gly Arg Phe Thr Val Ser Arg Asp Asn Ala Lys Asn Ser Leu Ser
            595                 600                 605
Leu Gln Met Asn Ser Leu Arg Ala Asp Asp Thr Ala Val Tyr Tyr Cys
        610                 615                 620
Ala Val Ser Pro Arg Gly Tyr Tyr Tyr Gly Leu Asp Leu Trp Gly
625                 630                 635                 640
Gln Gly Thr Thr Val Thr Val Ser Ser Glu Pro Lys Ser Cys Asp Lys
                    645                 650                 655
Thr His Thr Ala Glu Val Gln Leu Val Gln Ser Gly Gly Gly Leu Val
                660                 665                 670
Lys Pro Gly Gly Ser Leu Arg Leu Ser Cys Ala Ala Ser Gly Phe Thr
            675                 680                 685
Phe Ser Asp Tyr Tyr Met Ser Trp Ile Arg Gln Ala Pro Gly Lys Gly
        690                 695                 700
Leu Glu Trp Leu Ser Tyr Ile Ser Ser Asp Gly Ser Thr Ile Tyr Tyr
705                 710                 715                 720
Ala Asp Ser Val Lys Gly Arg Phe Thr Val Ser Arg Asp Asn Ala Lys
                    725                 730                 735
Asn Ser Leu Ser Leu Gln Met Asn Ser Leu Arg Ala Asp Asp Thr Ala
                740                 745                 750
Val Tyr Tyr Cys Ala Val Ser Pro Arg Gly Tyr Tyr Tyr Gly Leu
            755                 760                 765
Asp Leu Trp Gly Gln Gly Thr Thr Val Thr Val Ser Ser Ala Ser Thr
        770                 775                 780
Lys Gly Pro Ser Val Phe Pro Leu Ala Pro Ser Ser Lys Ser Thr Ser
785                 790                 795                 800
Gly Gly Thr Ala Ala Leu Gly Cys Leu Val Lys Asp Tyr Phe Pro Glu
                    805                 810                 815
Pro Val Thr Val Ser Trp Asn Ser Gly Ala Leu Thr Ser Gly Val His
                820                 825                 830
Thr Phe Pro Ala Val Leu Gln Ser Ser Gly Leu Tyr Ser Leu Ser Ser
            835                 840                 845
Val Val Thr Val Pro Ser Ser Ser Leu Gly Thr Gln Thr Tyr Ile Cys
        850                 855                 860
Asn Val Asn His Lys Pro Ser Asn Thr Lys Val Asp Lys Lys Val Glu
865                 870                 875                 880
Pro Lys Ser Cys

<210> SEQ ID NO 14
<211> LENGTH: 9
<212> TYPE: PRT
<213> ORGANISM: Artificial
<220> FEATURE:
<223> OTHER INFORMATION: Amino acid sequence MHC-1 HLA-A24 presentable
      peptide in MAGE-3

<400> SEQUENCE: 14

Thr Phe Pro Asp Leu Glu Ser Glu Phe
1               5
```

```
<210> SEQ ID NO 15
<211> LENGTH: 9
<212> TYPE: PRT
<213> ORGANISM: Artificial
<220> FEATURE:
<223> OTHER INFORMATION: Amino acid sequence MHC-1 HLA-A24 presentable
      peptide in MAGE-3

<400> SEQUENCE: 15

Ile Met Pro Lys Ala Gly Leu Leu Ile
1               5

<210> SEQ ID NO 16
<211> LENGTH: 16
<212> TYPE: PRT
<213> ORGANISM: Artificial
<220> FEATURE:
<223> OTHER INFORMATION: Amino acid sequence MHC-2 HLA-DP4 and HLA-DQ6
      presentable peptide in MAGE-3

<400> SEQUENCE: 16

Lys Lys Leu Leu Thr Gln His Phe Val Gln Glu Asn Tyr Leu Glu Tyr
1               5                   10                  15

<210> SEQ ID NO 17
<211> LENGTH: 802
<212> TYPE: PRT
<213> ORGANISM: Artificial
<220> FEATURE:
<223> OTHER INFORMATION: Amino acid sequence Hexa-11HAH5

<400> SEQUENCE: 17

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Leu
        35                  40                  45

Ser Tyr Ile Ser Ser Asp Gly Ser Thr Ile Tyr Tyr Ala Asp Ser Val
    50                  55                  60

Lys Gly Arg Phe Thr Val Ser Arg Asp Asn Ala Lys Asn Ser Leu Ser
65                  70                  75                  80

Leu Gln Met Asn Ser Leu Arg Ala Asp Asp Thr Ala Val Tyr Tyr Cys
                85                  90                  95

Ala Val Ser Pro Arg Gly Tyr Tyr Tyr Gly Leu Asp Leu Trp Gly
            100                 105                 110

Gln Gly Thr Thr Val Thr Val Ser Gly Gly Gly Ser Gly Gly
            115                 120                 125

Gly Gly Ser Gly Gly Ser Gln Leu Gln Leu Gln Glu Ser Gly Gly
    130                 135                 140

Gly Val Val Gln Pro Gly Arg Ser Leu Arg Leu Ser Cys Ala Ala Ser
145                 150                 155                 160

Gly Phe Thr Phe Ser Ser Tyr Gly Met His Trp Val Arg Gln Ala Pro
                165                 170                 175

Gly Lys Glu Arg Glu Gly Val Ala Val Ile Ser Tyr Asp Gly Ser Asn
            180                 185                 190

Lys Tyr Tyr Ala Asp Ser Val Lys Gly Arg Phe Thr Ile Ser Arg Asp
        195                 200                 205

Asn Ser Lys Asn Thr Leu Tyr Leu Gln Met Asn Ser Leu Arg Ala Glu
    210                 215                 220
```

-continued

```
Asp Thr Ala Val Tyr Tyr Cys Ala Gly Gly Ser Tyr Tyr Val Pro Asp
225                 230                 235                 240

Tyr Trp Gly Gln Gly Thr Leu Val Thr Val Ser Ser Gly Ser Thr Ser
            245                 250                 255

Gly Ser Gly Lys Ser Pro Gly Ser Gly Glu Gly Thr Lys Gly Glu Val
        260                 265                 270

Gln Leu Val Gln Ser Gly Gly Gly Leu Val Lys Pro Gly Gly Ser Leu
    275                 280                 285

Arg Leu Ser Cys Ala Ala Ser Gly Phe Thr Phe Ser Asp Tyr Tyr Met
290                 295                 300

Ser Trp Ile Arg Gln Ala Pro Gly Lys Gly Leu Glu Trp Leu Ser Tyr
305                 310                 315                 320

Ile Ser Ser Asp Gly Ser Thr Ile Tyr Tyr Ala Asp Ser Val Lys Gly
            325                 330                 335

Arg Phe Thr Val Ser Arg Asp Asn Ala Lys Asn Ser Leu Ser Leu Gln
        340                 345                 350

Met Asn Ser Leu Arg Ala Asp Asp Thr Ala Val Tyr Tyr Cys Ala Val
    355                 360                 365

Ser Pro Arg Gly Tyr Tyr Tyr Gly Leu Asp Leu Trp Gly Gln Gly
370                 375                 380

Thr Thr Val Thr Val Ser Ser Glu Phe Ala Lys Thr Thr Ala Pro Ser
385                 390                 395                 400

Val Tyr Pro Leu Ala Pro Val Leu Glu Ser Gly Ser Gly Gln Leu
            405                 410                 415

Gln Leu Gln Glu Ser Gly Gly Val Val Gln Pro Gly Arg Ser Leu
    420                 425                 430

Arg Leu Ser Cys Ala Ala Ser Gly Phe Thr Phe Ser Ser Tyr Gly Met
435                 440                 445

His Trp Val Arg Gln Ala Pro Gly Lys Glu Arg Glu Gly Val Ala Val
450                 455                 460

Ile Ser Tyr Asp Gly Ser Asn Lys Tyr Tyr Ala Asp Ser Val Lys Gly
465                 470                 475                 480

Arg Phe Thr Ile Ser Arg Asp Asn Ser Lys Asn Thr Leu Tyr Leu Gln
            485                 490                 495

Met Asn Ser Leu Arg Ala Glu Asp Thr Ala Val Tyr Tyr Cys Ala Gly
        500                 505                 510

Gly Ser Tyr Tyr Val Pro Asp Tyr Trp Gly Gln Gly Thr Leu Val Thr
    515                 520                 525

Val Ser Ser Gly Gly Gly Gly Ser Gly Gly Gly Gly Ser Gly Gly Gly
530                 535                 540

Gly Ser Glu Val Gln Leu Val Gln Ser Gly Gly Gly Leu Val Lys Pro
545                 550                 555                 560

Gly Gly Ser Leu Arg Leu Ser Cys Ala Ala Ser Gly Phe Thr Phe Ser
            565                 570                 575

Asp Tyr Tyr Met Ser Trp Ile Arg Gln Ala Pro Gly Lys Gly Leu Glu
        580                 585                 590

Trp Leu Ser Tyr Ile Ser Ser Asp Gly Ser Thr Ile Tyr Tyr Ala Asp
    595                 600                 605

Ser Val Lys Gly Arg Phe Thr Val Ser Arg Asp Asn Ala Lys Asn Ser
610                 615                 620

Leu Ser Leu Gln Met Asn Ser Leu Arg Ala Asp Asp Thr Ala Val Tyr
625                 630                 635                 640

Tyr Cys Ala Val Ser Pro Arg Gly Tyr Tyr Tyr Gly Leu Asp Leu
```

```
                    645                 650                 655
Trp Gly Gln Gly Thr Thr Val Thr Val Ser Ser Gly Ser Thr Ser Gly
            660                 665                 670

Ser Gly Lys Ser Pro Gly Ser Gly Glu Gly Thr Lys Gly Gln Leu Gln
        675                 680                 685

Leu Gln Glu Ser Gly Gly Gly Val Val Gln Pro Gly Arg Ser Leu Arg
    690                 695                 700

Leu Ser Cys Ala Ala Ser Gly Phe Thr Phe Ser Ser Tyr Gly Met His
705                 710                 715                 720

Trp Val Arg Gln Ala Pro Gly Lys Gly Leu Glu Trp Val Ala Val Ile
                725                 730                 735

Ser Tyr Asp Gly Ser Asn Lys Tyr Tyr Ala Asp Ser Val Lys Gly Arg
            740                 745                 750

Phe Thr Ile Ser Arg Asp Asn Ser Lys Asn Thr Leu Tyr Leu Gln Met
        755                 760                 765

Asn Ser Leu Arg Ala Glu Asp Thr Ala Val Tyr Tyr Cys Ala Gly Gly
    770                 775                 780

Ser Tyr Tyr Val Pro Asp Tyr Trp Gly Gln Gly Thr Leu Val Thr Val
785                 790                 795                 800

Ser Ser

<210> SEQ ID NO 18
<211> LENGTH: 5
<212> TYPE: PRT
<213> ORGANISM: Artificial
<220> FEATURE:
<223> OTHER INFORMATION: Linker peptide
<220> FEATURE:
<221> NAME/KEY: MISC_FEATURE
<222> LOCATION: (1)..(5)
<223> OTHER INFORMATION: this sequence may be repeated n times, where n
      is a positive integer

<400> SEQUENCE: 18

Gly Gly Gly Gly Ser
1               5

<210> SEQ ID NO 19
<211> LENGTH: 6
<212> TYPE: PRT
<213> ORGANISM: Artificial
<220> FEATURE:
<223> OTHER INFORMATION: Linker peptide
<220> FEATURE:
<221> NAME/KEY: MISC_FEATURE
<222> LOCATION: (1)..(6)
<223> OTHER INFORMATION: this sequence may be repeated n times, where n
      is a positive integer

<400> SEQUENCE: 19

Gly Ser Thr Ser Gly Ser
1               5

<210> SEQ ID NO 20
<211> LENGTH: 18
<212> TYPE: PRT
<213> ORGANISM: Artificial
<220> FEATURE:
<223> OTHER INFORMATION: Linker peptide

<400> SEQUENCE: 20

Gly Ser Thr Ser Gly Ser Gly Lys Pro Gly Ser Gly Glu Gly Ser Thr
1               5                   10                  15
```

Lys Gly

```
<210> SEQ ID NO 21
<211> LENGTH: 23
<212> TYPE: PRT
<213> ORGANISM: Artificial
<220> FEATURE:
<223> OTHER INFORMATION: Linker peptide

<400> SEQUENCE: 21
```

Glu Phe Ala Lys Thr Thr Ala Pro Ser Val Tyr Pro Leu Ala Pro Val
1               5                   10                  15

Leu Glu Ser Ser Gly Ser Gly
            20

```
<210> SEQ ID NO 22
<211> LENGTH: 10
<212> TYPE: PRT
<213> ORGANISM: Artificial
<220> FEATURE:
<223> OTHER INFORMATION: IgG1 Linker peptide

<400> SEQUENCE: 22
```

Glu Pro Lys Ser Cys Asp Lys Thr His Thr
1               5                   10

```
<210> SEQ ID NO 23
<211> LENGTH: 12
<212> TYPE: PRT
<213> ORGANISM: Artificial
<220> FEATURE:
<223> OTHER INFORMATION: IgG3 Linker peptide

<400> SEQUENCE: 23
```

Glu Leu Lys Thr Pro Leu Gly Asp Thr Thr His Thr
1               5                   10

```
<210> SEQ ID NO 24
<211> LENGTH: 7
<212> TYPE: PRT
<213> ORGANISM: Artificial
<220> FEATURE:
<223> OTHER INFORMATION: IgG4 Linker peptide

<400> SEQUENCE: 24
```

Glu Ser Lys Tyr Gly Pro Pro
1               5

```
<210> SEQ ID NO 25
<211> LENGTH: 4
<212> TYPE: PRT
<213> ORGANISM: Artificial
<220> FEATURE:
<223> OTHER INFORMATION: fluorescently labeled inhibitor for caspase 3/7
<220> FEATURE:
<221> NAME/KEY: MISC_FEATURE
<222> LOCATION: (1)..(1)
<223> OTHER INFORMATION: FAM attachment
<220> FEATURE:
<221> NAME/KEY: MISC_FEATURE
<222> LOCATION: (4)..(4)
<223> OTHER INFORMATION: FMK attachment

<400> SEQUENCE: 25
```

Asp Glu Val Asp
1

```
<210> SEQ ID NO 26
<211> LENGTH: 9
<212> TYPE: PRT
<213> ORGANISM: Artificial
<220> FEATURE:
<223> OTHER INFORMATION: MHC peptide

<400> SEQUENCE: 26

Thr Phe Pro Asp Leu Glu Ser Glu Lys
1               5

<210> SEQ ID NO 27
<211> LENGTH: 9
<212> TYPE: PRT
<213> ORGANISM: Artificial
<220> FEATURE:
<223> OTHER INFORMATION: MHC peptide

<400> SEQUENCE: 27

Ile Met Pro Lys Ala Gly Leu Leu Ile
1               5

<210> SEQ ID NO 28
<211> LENGTH: 16
<212> TYPE: PRT
<213> ORGANISM: Artificial
<220> FEATURE:
<223> OTHER INFORMATION: MHC peptide

<400> SEQUENCE: 28

Lys Lys Leu Leu Thr Gln His Phe Val Gln Glu Asn Tyr Leu Glu Tyr
1               5                   10                  15
```